(12) United States Patent
Kotaki et al.

(10) Patent No.: US 9,408,591 B2
(45) Date of Patent: Aug. 9, 2016

(54) ULTRASOUND DIAGNOSTIC DEVICE AND METHOD OF GENERATING AN INTERMEDIARY IMAGE OF ULTRASOUND IMAGE

(71) Applicant: HITACHI MEDICAL CORPORATION, Tokyo (JP)

(72) Inventors: Go Kotaki, Kumamoto (JP); Atsushi Miyamoto, Yokohama (JP); Kenji Nakahira, Yokohama (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 0 days.

(21) Appl. No.: 14/739,387

(22) Filed: Jun. 15, 2015

(65) Prior Publication Data

US 2015/0272552 A1 Oct. 1, 2015

Related U.S. Application Data

(63) Continuation of application No. 13/703,961, filed as application No. PCT/JP2011/061436 on May 18, 2011, now abandoned.

(30) Foreign Application Priority Data

Jul. 14, 2010 (JP) .................................. 2010-159771

(51) Int. Cl.
*A61B 8/08* (2006.01)
*A61B 8/00* (2006.01)
(Continued)

(52) U.S. Cl.
CPC ................. *A61B 8/5246* (2013.01); *A61B 8/14* (2013.01); *A61B 8/461* (2013.01); *A61B 8/462* (2013.01);
(Continued)

(58) Field of Classification Search
CPC .......... A61B 8/14; A61B 8/461; A61B 8/462; A61B 8/5207; A61B 8/5246; A61B 8/54; G06T 2207/10016; G06T 2207/10132; G06T 2207/30004; G06T 3/4053
See application file for complete search history.

(56) References Cited

U.S. PATENT DOCUMENTS 5,495,846 A   3/1996   Uehara et al.
6,210,328 B1  4/2001   Robinson et al.
(Continued)

FOREIGN PATENT DOCUMENTS

JP   H05-038340 A   2/1993
(Continued)

OTHER PUBLICATIONS

Torfinn Taxt, Superresolution of Ultrasound Images Using the First and Second Harmonic Signal, IEEE Transactions on Ultrasonics, Ferroelectric, and Frequency Control, Feb. 2004, pp. 163-175, vol. 51, No. 2.

*Primary Examiner* — Michael Rozanski
(74) *Attorney, Agent, or Firm* — Baker Botts L.L.P.

(57) ABSTRACT

In order to acquire high resolution ultrasound images while maintaining an appropriate frame rate in ultrasound diagnostic devices, the disclosed method generates high resolution ultrasound images by performing image reconstruction on the basis of multiple ultrasound frame images captured along a time series and the magnitudes of positional shifts, or forms high resolution ultrasound images by performing image reconstruction on the basis of multiple ultrasound frame images acquired by controlling the ultrasound probe and varying scan orientation or scan focal length frame by frame.

14 Claims, 18 Drawing Sheets

(51) Int. Cl.
*A61B 8/14* (2006.01)
*G06T 3/40* (2006.01)

(52) U.S. Cl.
CPC .............. *A61B 8/5207* (2013.01); *A61B 8/54* (2013.01); *G06T 3/4053* (2013.01); *G06T 2207/10016* (2013.01); *G06T 2207/10132* (2013.01); *G06T 2207/30004* (2013.01)

(56) References Cited

U.S. PATENT DOCUMENTS

| 2004/0225221 | A1 | 11/2004 | Olsson |
| 2005/0063611 | A1 | 3/2005 | Toki et al. |
| 2009/0048516 | A1 | 2/2009 | Yoshikawa et al. |
| 2009/0306505 | A1 | 12/2009 | Yoshikawa et al. |
| 2012/0041312 | A1 | 2/2012 | Nakahira et al. |

FOREIGN PATENT DOCUMENTS

| JP | H05-220138 A | 8/1993 |
| JP | H08-307771 A | 11/1996 |
| JP | 2002-526225 A | 8/2002 |
| JP | 2002-526226 A | 8/2002 |
| JP | 2003-061955 A | 3/2003 |
| JP | 2005-095328 A | 4/2005 |
| JP | 2009-039428 A | 2/2009 |
| JP | 2010-057010 A | 3/2010 |
| WO | WO 2006/123742 A1 | 11/2006 |
| WO | WO 2007/097108 A1 | 8/2007 |

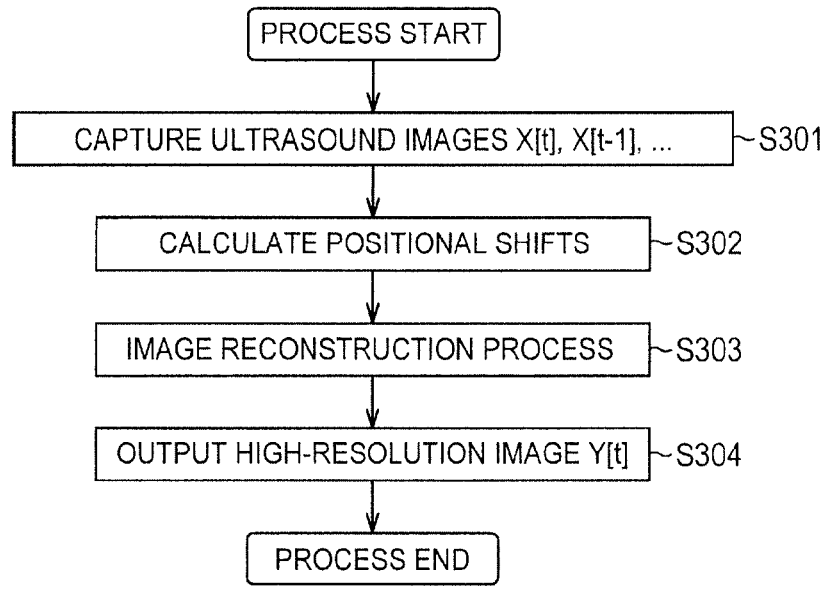
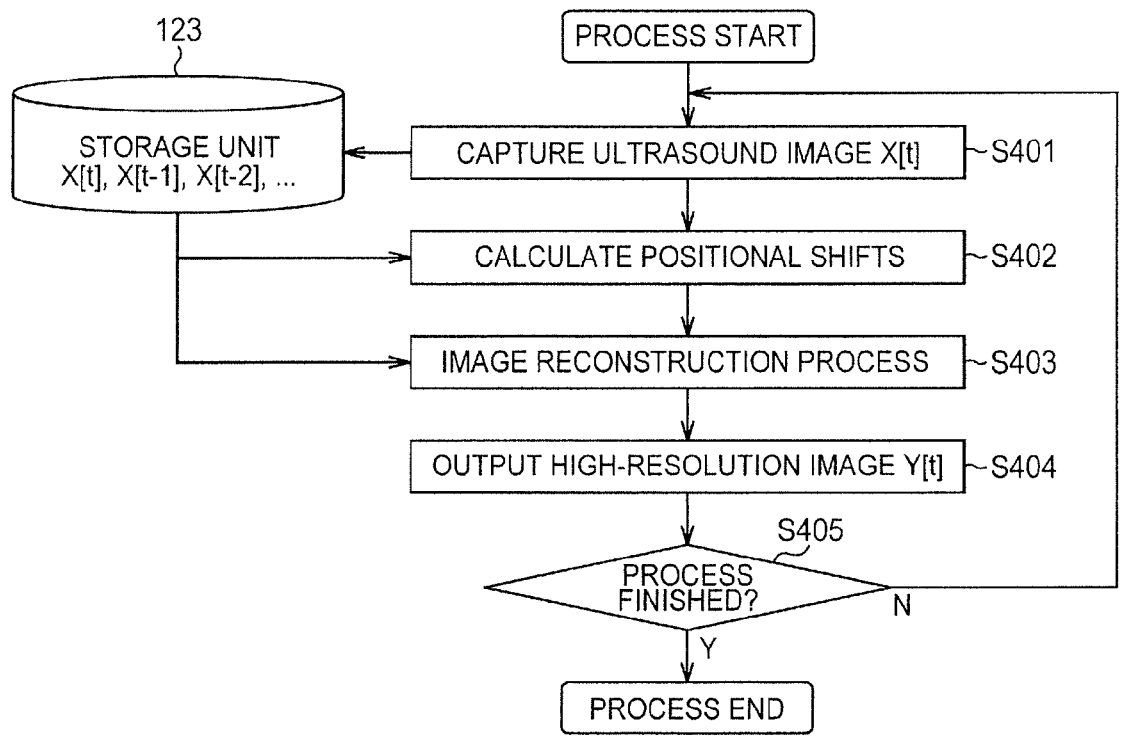

ULTRASOUND DIAGNOSTIC DEVICE AND METHOD OF GENERATING AN INTERMEDIARY IMAGE OF ULTRASOUND IMAGE

CROSS REFERENCE TO RELATED APPLICATIONS

This application is a continuation of U.S. patent application Ser. No. 13/703,961, filed on Dec. 13, 2012, which is a U.S. National Stage patent application under 35 U.S.C. §371 of International Patent Application No. PCT/JP2011/061436, filed on May 18, 2011, which claims priority of Japanese Patent Application No. 2010-159771, filed on Jul. 14, 2010, the entire contents of each of which are hereby incorporated by reference.

TECHNICAL FIELD

The present invention relates to an ultrasound diagnostic device which acquires images by transmitting and receiving an ultrasonic wave to/from a test object. In particular, the present invention relates to an ultrasound image reconstruction method, an ultrasound image reconstruction device and an ultrasound diagnostic device for conducting a process for enhancing the spatial resolution or the temporal resolution to the acquired images by means of image processing.

BACKGROUND ART

Ultrasound diagnostic devices are used for the inspection of various parts in the body such as the abdomen and the heart. The ultrasound diagnostic devices, having advantages like harmlessness to living tissues in contrast to X-ray inspection, simple and easy operation, and possibility of video observation in real time, are widely used today. In the ultrasound diagnostic device, an ultrasound probe emits an ultrasonic wave toward the test object and receives a reflected wave from a tissue inside the test object. Based on the received reflected wave, an ultrasound image of the tissue (test object) is displayed on a monitor. In the capturing of ultrasound images, it is possible to acquire two-dimensional images or three-dimensional images in real time by scanning a converged ultrasonic wave (ultrasound beam converged in a particular direction) with respect to the azimuth direction.

Since doctors have to find and diagnose minute lesions (tumors, etc.) by observing ultrasound images by use of ultrasound diagnostic devices, the ability to acquire ultrasound images with high visibility is required of the ultrasound diagnostic devices. Further, the definition of display monitors is improving fast especially in these years, and thus enhancement of the resolution of ultrasound images is being requested accordingly.

To meet the above request, it is possible to acquire a high-resolution ultrasound image by increasing the resolution with respect to the scan azimuth direction by increasing the number of scans of the ultrasound probe per frame. It is also possible to generate a high-resolution image by conducting a deconvolution process to an acquired image for one frame (one frame image) as described in Patent Literature 1. A technique described in Non-patent Literature 1 is known as an example of the deconvolution process, in which an ideal ultrasound image with no deterioration is estimated from an acquired ultrasound image through the modeling of image blurring caused by the aberration of the ultrasound beam and image deterioration caused by the sampling.

In a method described in Patent Literature 2, the body motion of the object under consideration (considered object) in the imaging plane is measured by using ultrasound images. Information varying with time (the shape of the considered object, tissue degradation, etc.) is visualized and displayed by adding up or subtracting time-line images while compensating for the measured body motion.

PRIOR ART LITERATURE

Patent Literature

Patent Literature 1: JP-2005-95328-A
Patent Literature 2: WO 2006/123742

Non-Patent Literature

Non-patent Literature 1: T. Taxt, R. Jirik: Superresolution of ultrasound images using the first and second harmonic signal, IEEE Trans. Ultrasonics, Ferroelectrics, and Frequency Control, Vol. 51, No. 2, pp. 163-175, 2004

SUMMARY OF THE INVENTION

Problem to be Solved by the Invention

However, even though the above method increasing the number of scans per frame is capable of acquiring high-resolution ultrasound images, the method involves a problem of decreasing the display frame rate since the time necessary for acquiring one frame image increases due to an increase in the propagation time of the ultrasonic wave. This leads to an insufficient frame rate and a hitch in the diagnosis especially in the observation of fast-moving parts (e.g., heart). Meanwhile, some problems have been known in regard to the aforementioned deconvolution process, such as occurrence of unnatural artifacts to images having much noise. Therefore, the resolution enhancement effect cannot be expected so much when the acquired ultrasound image includes much noise.

The method described in the Patent Literature 2 is capable of extracting and visualizing information varying with time from time-line images. However, the Patent Literature 2 has not described a method for acquiring high-resolution ultrasound images.

As described above, it has been difficult in the conventional technology to acquire high-resolution ultrasound images while maintaining an appropriate frame rate.

It is therefore the primary object of the present invention to resolve the above problem with the conventional technology and provide an ultrasound image reconstruction method capable of acquiring high-resolution ultrasound images while maintaining an appropriate frame rate, a device for implementing the ultrasound image reconstruction method, and an ultrasound diagnostic device employing such a device.

Means for Solving the Problem

To achieve the above object, the present invention provides an ultrasound image reconstruction method for reconstructing an ultrasound image of a sample by processing ultrasound images acquired from a signal generated by scanning the sample with an ultrasound signal by use of an ultrasound probe and receiving a reflected wave from the sample, comprising the steps of: extracting an ultrasound frame image at a certain time point and an ultrasound frame image at a time point before the certain time point from a series of ultrasound frame images constituting the ultrasound images acquired by the imaging; calculating magnitudes of positional shifts between the extracted ultrasound frame image at the certain time point and the extracted ultrasound frame image at the time point before the certain time point; and reconstructing a composite ultrasound image for one frame by compensating for the positional shifts between the extracted ultrasound frame image at the certain time point and the extracted ultrasound frame image at the time point before the certain time point by use of information on the calculated magnitudes of positional shifts and merging the extracted ultrasound frame image at the certain time point and the extracted ultrasound frame image at the time point before the certain time point after undergoing the positional shift compensation together. By successively repeating the above process, high-resolution ultrasound images, having higher resolution than the ultrasound images acquired by imaging the sample, are generated without decreasing the frame rate from that of the ultrasound images.

To achieve the above object, an ultrasound image reconstruction device in accordance with the present invention is configured to comprise: reception circuit means which receives a reflected wave signal generated by scanning a sample with an ultrasound probe and receiving a reflected wave from the sample; image generating means which generates ultrasound images from the reflected wave signal received by the reception circuit means; image processing means which executes a reconstruction process to the ultrasound images generated by the image generating means; and display means which displays an ultrasound image obtained by the reconstruction process by the image processing means on a screen. The image processing means extracts an ultrasound frame image at a certain time point and an ultrasound frame image at a time point before the certain time point from a series of ultrasound frame images constituting the ultrasound images generated by the image generating means, calculates magnitudes of positional shifts between the extracted ultrasound frame image at the certain time point and the extracted ultrasound frame image at the time point before the certain time point, and reconstructs a composite ultrasound image for one frame by compensating for the positional shifts between the extracted ultrasound frame image at the certain time point and the extracted ultrasound frame image at the time point before the certain time point by use of information on the calculated magnitudes of positional shifts and merging the extracted ultrasound frame image at the certain time point and the extracted ultrasound frame image at the time point before the certain time point after undergoing the positional shift compensation together. By successively repeating the above process, high-resolution ultrasound images, having higher resolution than the ultrasound images generated by the image generating means, are reconstructed without decreasing the frame rate from that of the ultrasound images.

To achieve the above object, an ultrasound diagnostic device in accordance with the present invention is configured to comprise: an ultrasound probe which scans a sample with an ultrasound signal and receives a reflected wave from the sample; a drive circuit unit which generates a high-frequency signal for driving the ultrasound probe; an ultrasound image reconstruction processing unit which generates ultrasound images by processing the reflected wave received by the ultrasound probe and executes a reconstruction process to the generated ultrasound images; and a control/storage/processing unit which controls the entire device while storing and processing data. The ultrasound image reconstruction processing unit includes reception circuit means which receives the reflected wave signal received by the ultrasound probe, image generating means which generates ultrasound images from the reflected wave signal received by the reception circuit means, image processing means which executes the reconstruction process to the ultrasound image generated by the image generating means, and display means which displays an ultrasound image obtained by the reconstruction process by the image processing means on a screen. The image processing means extracts an ultrasound frame image at a certain time point and an ultrasound frame image at a time point before the certain time point from a series of ultrasound frame images constituting the ultrasound images generated by the image generating means, calculates magnitudes of positional shifts between the extracted ultrasound frame image at the certain time point and the extracted ultrasound frame image at the time point before the certain time point, and reconstructs a composite ultrasound image for one frame by compensating for the positional shifts between the extracted ultrasound frame image at the certain time point and the extracted ultrasound frame image at the time point before the certain time point by use of information on the calculated magnitudes of positional shifts and merging the extracted ultrasound frame image at the certain time point and the extracted ultrasound frame image at the time point before the certain time point after undergoing the positional shift compensation together. By successively repeating the above process, high-resolution ultrasound images, having higher resolution than the ultrasound images generated by the image generating means, are reconstructed without decreasing the frame rate from that of the ultrasound images.

Effect of the Invention

According to the present invention, by employing the image reconstruction process by use of multiple frame images, the resolution enhancement of the ultrasound images is realized without decreasing the frame rate. Further, the resolution enhancement effect can be increased by employing a suitable ultrasound probe scanning method for the image reconstruction process. Consequently, high-resolution ultrasound images can be acquired while maintaining an appropriate frame rate. Especially, improvement in the visibility of lesions moving fast can be expected.

BRIEF DESCRIPTION OF THE DRAWINGS

FIG. 3 is a flow chart for executing an image reconstruction process by using multiple frame images and magnitudes of positional shifts.

FIG. 4 is a flow chart showing a case where the flow of FIG. 3 is equipped with a storage device.

DESCRIPTION OF THE PREFERRED EMBODIMENTS

Figure 1:
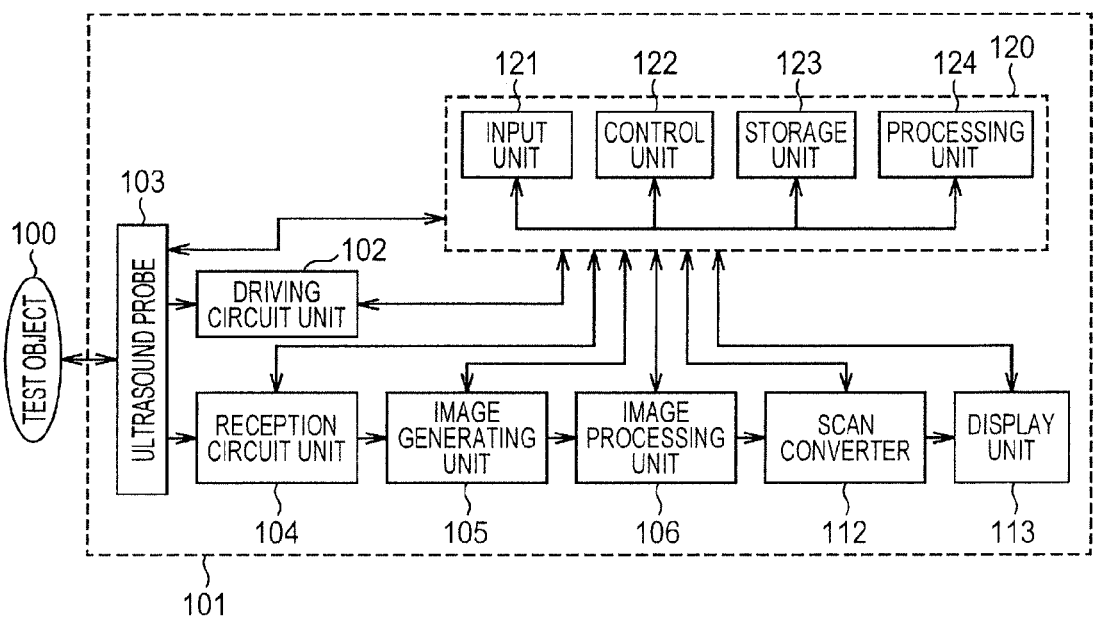
FIG. 1 is a block diagram showing the configuration of an ultrasound diagnostic device for implementing the present invention.

The present invention resolves the aforementioned problem by employing an ultrasound image reconstruction method including the processes described below, an ultrasound image reconstruction device equipped with the image reconstruction process, and an ultrasound diagnostic device equipped with the image reconstruction process.

(1) The first case of this invention is that one high-resolution ultrasound image is generated from a plurality of ultrasound images acquired along a time series (ultrasound image group) by employing an image reconstruction process. Specifically, an image reconstruction process suppressing the effect of noise is realized by generating one high-resolution ultrasound image by using multiple frames of ultrasound images (multiple ultrasound frame images) without executing the image reconstruction process by using one frame of ultrasound image (one ultrasound frame image). Further, by the use of multiple frame images for the image reconstruction process, complementary synthesis of the image information on each frame becomes possible, achieving excellent effect in the resolution enhancement.

Concretely, in the present invention, an ultrasound image at a particular temporal phase as the object of the processing (processing object image) and ultrasound images to be inputted to the image reconstruction process (input images) are extracted first. Subsequently, magnitudes of positional shifts are calculated for the processing object image and each of the input images. A high-resolution processing object image is generated from the input ultrasound images and the magnitudes of positional shifts by employing the image reconstruction process. Specifically, by previously calculating the magnitudes of positional shifts between frames and using the calculated magnitudes of positional shifts for the image reconstruction process, influence of image blurring that is caused by positional shifts occurring in the simple frame averaging (arithmetic mean) can be suppressed. Further, region splitting is conducted to the processing object image and a weighting parameter of the image reconstruction process is set for each of the regions acquired by the splitting.

The region splitting can either be conducted in a manually given region or performed automatically based on the magnitudes of positional shifts. Incidentally, this processing is characterized in that an image in a region (regional image) having a larger weighting parameter is incorporated more into the result of the image reconstruction process. For example, a point where the magnitude of positional shift is large has a high probability that parts around the point have deformed significantly, and thus there are cases where executing the image reconstruction process by compensating for the deformation is difficult. In such cases, regions in which the positional shift compensation is difficult are assigned small weighting parameters according to the present invention. In such regions, the image data of the processing object image becomes dominant. Thus, according to the present invention, regions in which the image reconstruction process is highly effective can be extracted automatically and the resolution enhancement can be performed on such regions even in the observation of a part moving fast (e.g., heart).

(2) The second case of this invention is that by using ultrasound images acquired by conducting the image capturing at the image acquisition intervals and the magnitudes of positional shifts between images calculated by a method similar to the above case (1), estimating an ultrasound image that is supposed to be acquired by conducting the image capturing with timing shifted from the capturing timing of the processing object image (ultrasound image as the object of the image reconstruction process) by a time shorter than the image acquisition interval (time interval specified along the time series). While the above case (1) is a process for increasing the spatial resolution, this case (2) is a process for increasing the resolution in the temporal direction by estimating frame images between the acquired frame images. According to this case, the frame rate can be increased without decreasing the number of scans per frame (i.e., without deteriorating the spatial resolution of images).

(3) The third case of this invention is that since the image reconstruction process using multiple frames is a process of complementarily synthesizing the image information on each frame as mentioned in the explanation of the above case (1), the resolution enhancement effect is weak if substantially identical images are inputted to the image reconstruction process. In contrast, an aspect of the present case is characterized in that ultrasound images differing in the scan condition are acquired by controlling the ultrasound probe and the image reconstruction process is executed by using the ultrasound images acquired under different scan conditions. Specifically, changing the scan condition allows the ultrasound images to contain a substantial amount of complementary information, by which the resolution enhancement effect by the image reconstruction process can be increased. Usable scan conditions may include the interlace method which alternately switches between image acquisition exclusively in even-numbered scan orientations and image acquisition exclusively in odd-numbered scan orientations frame by frame. In regions in which the movement is small, the resolution enhancement can be achieved just by simply overlaying images acquired by the interlace method.

In contrast, when the movement of the test object is large (e.g., heart), an image shift called "jitter" can occur at the interfaces between images. Also for such jitter, a process of synthesizing seamless frame images can be realized by conducting a compensation process by using the magnitudes of positional shifts. This method can be implemented also for three or more frames in a similar manner.

A method switching the scan focal length frame by frame can also be employed as another scan method. Specifically, if the focal point of the ultrasound beam during the scan is restricted to a particular position, the images of the other parts are blurred even though a sharp and clear image can be acquired for the particular position where the beam is converged. Therefore, the tight-focused image area can be increased by merging (combining) multiple ultrasound images acquired by changing the scan focal length frame by frame. Incidentally, this method is capable of increasing the spatial resolution of images without deteriorating the frame rate since the number of scans per frame is not increased in this method.

(4) The fourth case of this invention is that the cycle of the movement of the part as the observation object is acquired, the image reconstruction process is employed for ultrasound images (ultrasound image group) acquired by executing the image capturing for a time range (image capturing time range) longer than or equal to twice the cycle, and ultrasound images within a time range shorter than the image capturing time range are generated by the image reconstruction process. In this case, the ultrasound probe is controlled so that each image in the ultrasound image group (object image) and an image captured substantially the cycle before the capturing time of the object image (past object image) are captured under different scan conditions. Since a part like the heart repeats periodical movement, ultrasound images of such a part captured at times at the same temporal phase in the repeated cycles become substantially identical with each other. Thus, for the same reason as that described in the explanation of the above case (3), the resolution enhancement effect cannot be expected so much even if a lot of substantially identical images are inputted to the image reconstruction process.

In contrast, the image capturing of the aforementioned object image and that of the aforementioned past object image in the present case are carried out under different scan conditions by changing the scan condition, by which the ultrasound images are allowed to contain a substantial amount of complementary information and the resolution enhancement effect by the image reconstruction process can be increased. The scan orientation, the scan range, the scan focal length, etc. may be changed as the scan condition.

Referring now to the drawings, a description will be given in detail of a preferred embodiment in accordance with the present invention.

First, the configuration of an ultrasound diagnostic device in accordance with the present invention will be described below with reference to FIGS. 1 and 2.

Figure 2:
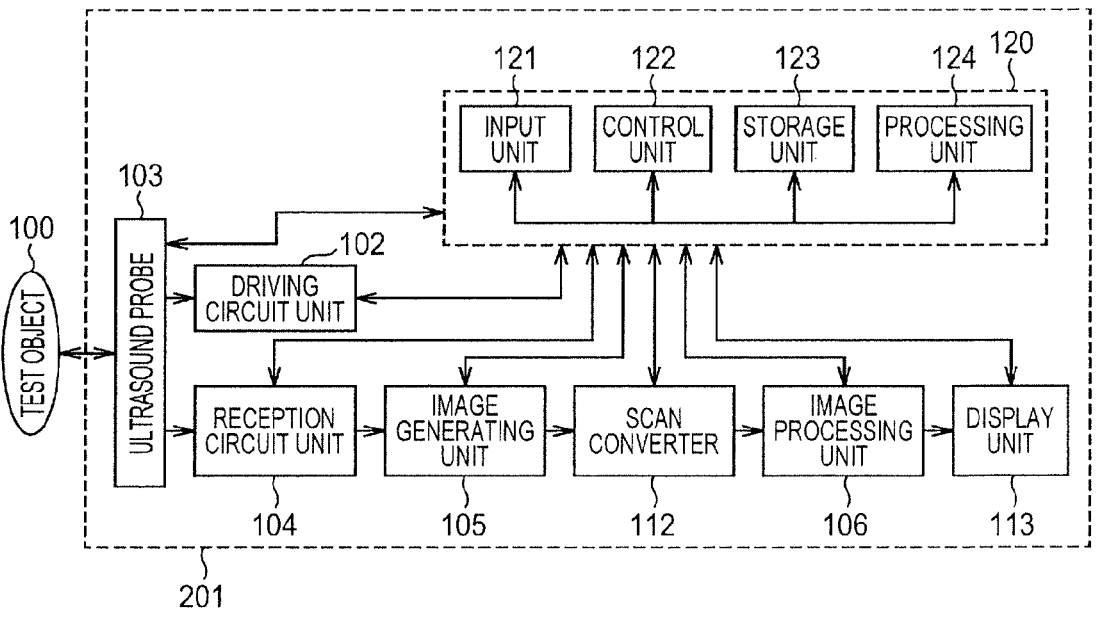
FIG. 2 is a block diagram showing the configuration of another ultrasound diagnostic device for implementing the present invention.

FIG. 1 is a block diagram showing an example of the configuration of the ultrasound diagnostic device 101. The ultrasound diagnostic device 101 comprises an ultrasound probe 103 which transmits and receives ultrasound signals, a driving circuit 102 which generates a driving signal to be inputted to the ultrasound probe 103, a reception circuit 104 which conducts amplification and A/D conversion to received signals, an image generating unit 105 which generates an image in which a scan line signal sequence of the ultrasound scan is arranged in a two-dimensional array, an image processing unit 106 which performs image processing such as the image reconstruction process, a scan converter 112 which conducts a coordinate transformation process and an interpolation process to images represented by the scan line signal sequences, a display unit 113 which displays images generated by the scan converter, and a control/storage/processing unit 120 which controls all the above components while storing and processing data.

The ultrasound probe 103 transmits an ultrasound signal based on the driving signal toward a test object 100. The ultrasound probe 103 also receives a reflected wave from the test object 100 in response to the signal transmission and converts the received reflected wave into an electric reception signal. There are various types of ultrasound probes 103, such as the so-called linear type, convex type, sector type and radial type. When the ultrasound probe 103 of the convex type is used, for example, an image in a rectangular shape is converted by the scan converter 112 into an image in a fan-like shape. The control/storage/processing unit 120 includes an input unit 121, a control unit 122, a storage unit 123 and a processing unit 124. From the input unit 121, information on the timing for starting the image generation, parameters regarding the image generation, etc. are inputted.

The control unit 122 controls the operations of the driving circuit 102, the ultrasound probe 103, the reception circuit 104, the image processing unit 106, and so forth. The storage unit 123 stores the received signals (reception signals), the images generated by the image generating unit 105, images generated by calculation by the image processing unit 106, display images outputted by the scan converter 112, etc. The processing unit 124 performs a shaping process on the electric signal to be inputted to the ultrasound probe 103, a process of adjusting the brightness and the contrast in the displaying of the images, etc.

In the configuration described above, the ultrasound probe 103 transmits the ultrasound signal based on the driving signal controlled by the control unit 122 of the control/storage/processing unit 120 to the test object 100, receives the reflected wave from the test object 100 in response to the signal transmission, and converts the received reflected wave into the electric reception signal. Subsequently, the reception circuit 104 conducts amplification and A/D conversion to the reception signal converted to the electric signal. The image generating unit 105 generates images by processing the digital signal acquired by the A/D conversion and inputs the generated images to the image processing unit 106. The image processing unit 106 executes the image reconstruction process to the inputted images, by which a high-resolution output image is acquired.

Further, the scan converter 112 conducts the image coordinate transformation process and the interpolation process to the output image and thereby generates an image. Incidentally, the configuration of the ultrasound diagnostic device 101 is not restricted to this example. For example, the image processing unit 106 may also be arranged after the scan converter 112 as illustrated in the configuration of an ultrasound diagnostic device 201 in FIG. 2.

Figure 21:
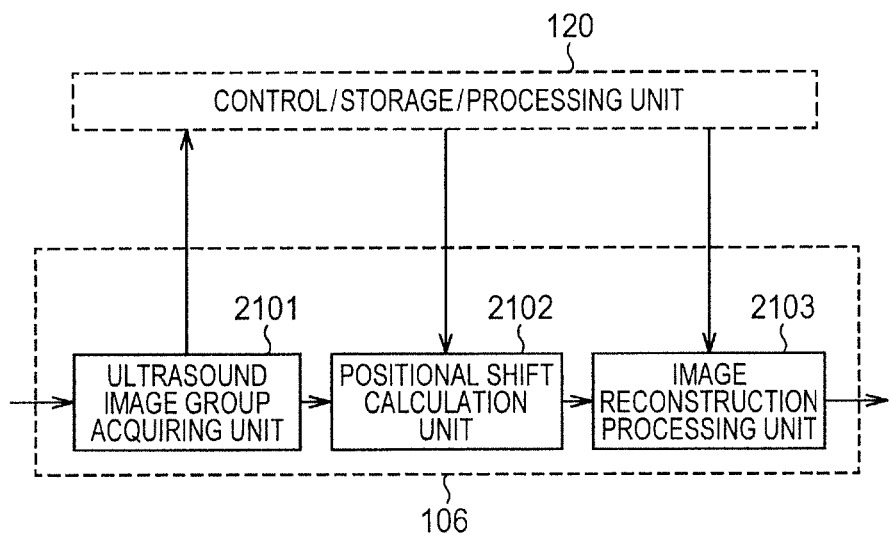
FIG. 21 is a block diagram showing the configuration of an image reconstruction processing device for implementing the present invention.
Figure 22:
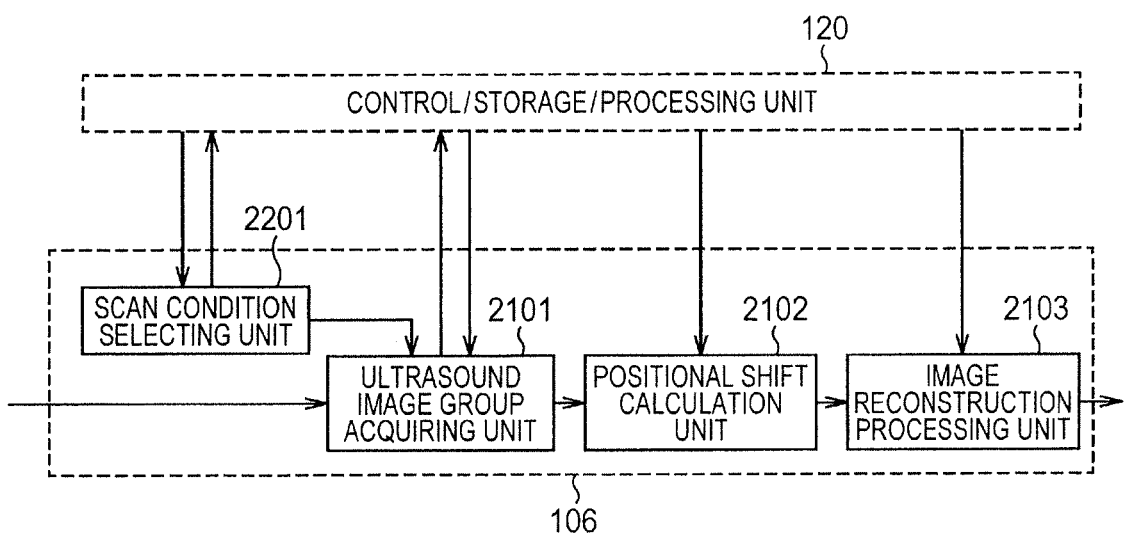
FIG. 22 is a block diagram showing the configuration of another image reconstruction processing device for implementing the present invention.

FIGS. 21 and 22 are block diagrams showing the internal processing by the image processing unit 106. The image data outputted from the image generating unit 105 is first inputted to an ultrasound image group acquiring unit 2101, by which a frame image of the inputted image data is stored in the storage unit 123 of the control/storage/processing unit 120 and is also transmitted to a positional shift calculation unit 2102. The frame image transmitted from the ultrasound image group acquiring unit 2101 and a past frame image group (past frame images) stored in the storage unit 123 are inputted to the positional shift calculation unit 2102, by which the magnitudes of positional shifts are calculated.

Subsequently, the past frame image group stored in the storage unit 123, the current frame image and the magnitudes of positional shifts are inputted to an image reconstruction processing unit 2103, by which a high-resolution current frame image is outputted. FIG. 22 shows another example of the internal processing by the image processing unit 106. In the example of FIG. 22, the scan orientation or the focal length of the ultrasound beam is set by a scan condition selecting unit 2201 and the ultrasound images are captured according to the scan condition. Thereafter, the image reconstruction process is executed similarly to the processing shown in FIG. 21.

Example 1

An example of the image reconstruction process in the present invention will be described below referring to a flow chart of FIG. 3. First, an ultrasonic wave is emitted toward the test object 100 by use of the ultrasound probe 103 and a reflected wave from a tissue inside the test object 100 is detected by the ultrasound probe 103. The detected signal is sent to the image generating unit 105 via the reception circuit 104 and processed by the image generating unit 105, by which ultrasound images (ultrasound image group) X[t], X[t−1], X[t−2], . . . captured along a time series are acquired (S301). Here, X[t] represents an ultrasound image captured last, and X[t−1], X[t−2], . . . represent ultrasound images captured before the ultrasound image X[t].

The ultrasound images acquired along the time series are sent to the image processing unit 106 and inputted to the ultrasound image group acquiring unit 2101 of the image processing unit 106, by which each of the frame images is stored in the storage unit 123 of the control/storage/processing unit 120. Subsequently, the positional shift calculation unit 2102 extracts an ultrasound image as the object of the image reconstruction process (processing object image) from the ultrasound images outputted from the ultrasound image group acquiring unit 2101 and also extracts ultrasound images to be inputted to the image reconstruction process (input images (input image group)) from the frame images stored in the storage unit 123 of the control/storage/processing unit 120.

For example, the ultrasound image X[t] outputted from the ultrasound image group acquiring unit 2101 is extracted as the processing object image, and the ultrasound images X[t], X[t−1] and X[t−2] stored in the storage unit 123 are extracted as the input image group. Subsequently, the positional shift calculation unit 2102 calculates the magnitudes of positional shifts between the processing object image and each image in the input image group (S302). The magnitudes of positional shifts can be calculated by employing common algorithm for the positional shift calculation such as the optical flow method and the block matching method. Then, a high-resolution processing object image Y[t] is generated by the image reconstruction processing unit 2103 from the input image group and the calculated magnitudes of positional shifts (S303) and displayed on the screen of the display unit 113 (S304).

By previously calculating the magnitudes of positional shifts between frames and using the calculated magnitudes of positional shifts for the image reconstruction process as above, image blurring effect that is caused by positional shifts occurring in the simple frame averaging (arithmetic mean) can be suppressed. For the image reconstruction process using a plurality of images, a reconstruction-based super-resolution process, estimating the high-resolution image by minimizing the value of the following expression (1), can be employed, for example.

$$L(Y)=\Sigma_{i=1}^{N}|DF_iS_iY-X_i|+\gamma(|Y-T_xY|+|Y-T_yY|) \quad (1)$$

In the above expression (1), "Xi" denotes the i-th image in the input image group (including N images), "Y" denotes the high-resolution image generated by the image reconstruction process, "Si" denotes an operation (effect) representing the positional shifts of the i-th image, "Fi" denotes an operation (effect) representing the blurring of the i-th image, "D" denotes an operation (effect) due to the quantization, "Tx" denotes an operation (effect) shifting the image in the X direction by 1 pixel, and "Ty" denotes an operation (effect) shifting the image in the Y direction by 1 pixel.

The first term in the expression (1) is a term representing the error between the high-resolution image Y observed while being affected by various image deteriorating factors and each image Xi. The second term is a term stabilizing the reconstructed high-resolution image Y to have smooth luminance values. The stabilization term is adjusted by the parameter γ. By generating one high-resolution ultrasound image by using multiple frames of ultrasound images (multiple ultrasound frame images) as described above instead of executing the image reconstruction process by using one frame of ultrasound image (one ultrasound frame image), an image reconstruction process suppressing the effect of noise is realized. Further, by the use of multiple frame images, complementary synthesis of the image information on each frame becomes possible, achieving excellent effect in the resolution enhancement.

Figure 23:
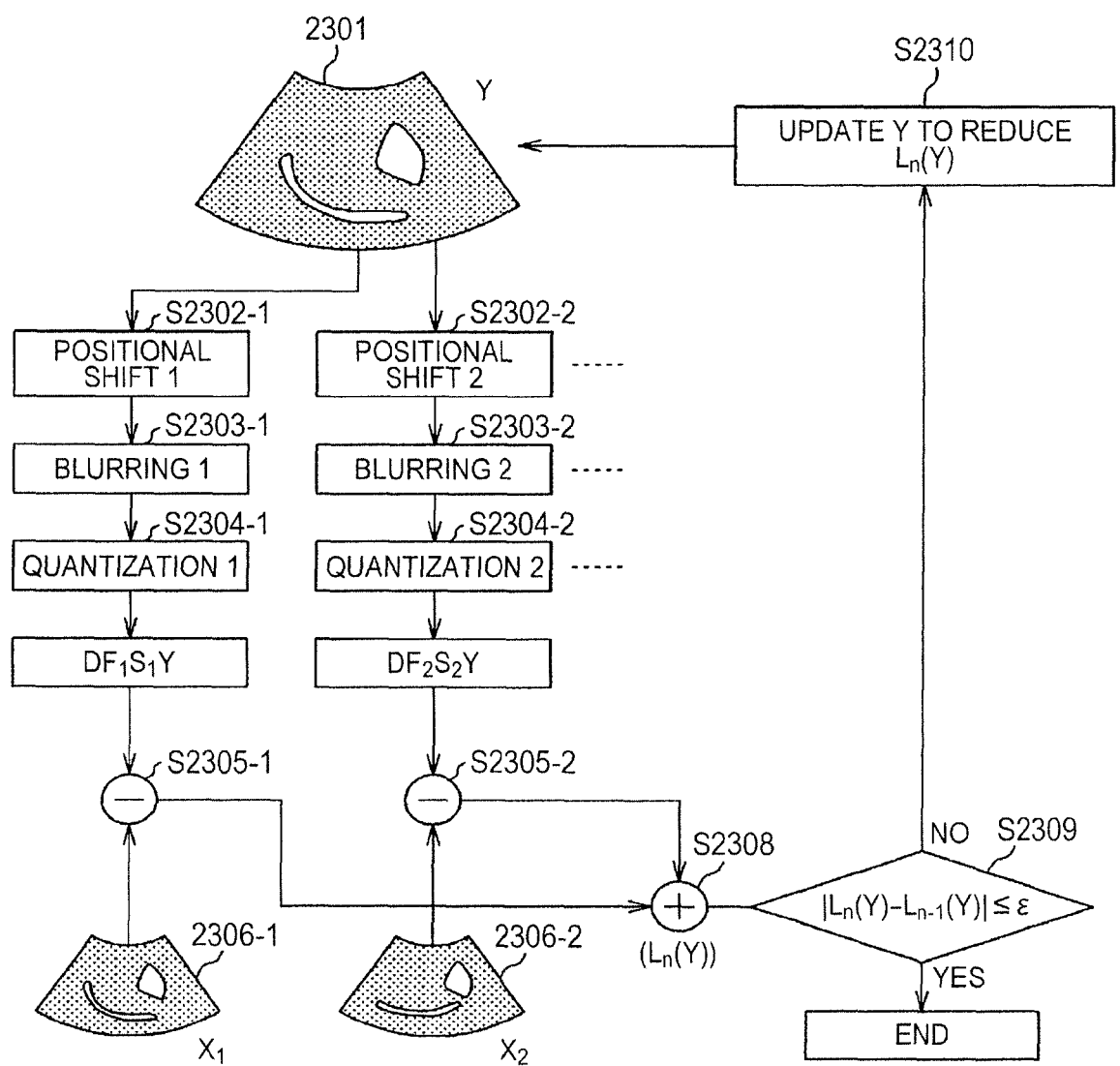
FIG. 23 is a flow chart of the image reconstruction process using multiple frame images.

The flow of the image reconstruction process will be explained below referring to FIG. 23. The reference character 2301 represents the high-resolution ultrasound image Y which should be estimated by the image reconstruction process. The reference characters 2306-1 and 2306-2 represent the acquired first and second frames of ultrasound images (first and second ultrasound frame images), respectively. By using the calculated magnitudes of positional shifts of the first and second frames, the positional shift operation is performed on the image 2301 (S2302-1, S2302-2). Subsequently, the image blurring operation due to the image capturing is performed (S2303-1, S2303-2) and the image quantization operation is performed (S2304-1, S2304-2). The difference between each image DFiSiY acquired by the above process and each captured image Xi is calculated (S2305-1, S2305-2) and the sum Ln(Y) of the differences is calculated (S2308). Then, the image Y is updated so as to reduce the value of Ln(Y) (S2310). By repeating the above process until the difference between the currently obtained Ln(Y) and the previously obtained Ln−1(Y) falls within a prescribed value, one high-resolution ultrasound image can be generated from multiple frames of ultrasound images.

Incidentally, the process flow shown in FIG. 3 can also be performed as shown in FIG. 4 in the actual processing. In the flow shown in FIG. 4, the ultrasound images of the test object 100 generated by the image generating unit 105 are previously stored in the storage unit 123 of the control/storage/processing unit 120 and the stored ultrasound images X[t], X[t−1] and X[t−2] are used for the image reconstruction process, for example. It is also possible to generate high-resolution video (motion video) data by conducting the resolution enhancement offline to the images accumulated in the storage unit 123 all at once.

The flow of the process shown in FIG. 4 will be explained below. First, an ultrasonic wave is emitted toward the test object 100 by use of the ultrasound probe 103 and a reflected wave from a tissue inside the test object 100 is detected by the ultrasound probe 103. The detected signal is sent to the image generating unit 105 via the reception circuit 104 and processed by the image generating unit 105, by which ultrasound images X[t], X[t−1], X[t−2], . . . are acquired (S401). The acquired ultrasound images X[t], X[t−1], X[t−2], . . . are stored in the storage unit 123 of the control/storage/processing unit 120.

Subsequently, the ultrasound image group acquiring unit 2101 of the image processing unit 106 acquires the processing object image and the input image group (input images) from the ultrasound images X[t], X[t−1], X[t−2], . . . stored in the storage unit 123, and the positional shift calculation unit 2102 calculates the magnitudes of positional shifts between the acquired processing object image and each image in the acquired input image group (S402).

Then, a high-resolution processing object image Y[t] is generated by the image reconstruction processing unit 2103 from the input image group and the calculated magnitudes of positional shifts (S403) and displayed on the screen of the display unit 113 (S404).

The above sequence of steps is executed repeatedly until the image capturing is finished (S405).

Figure 5A:
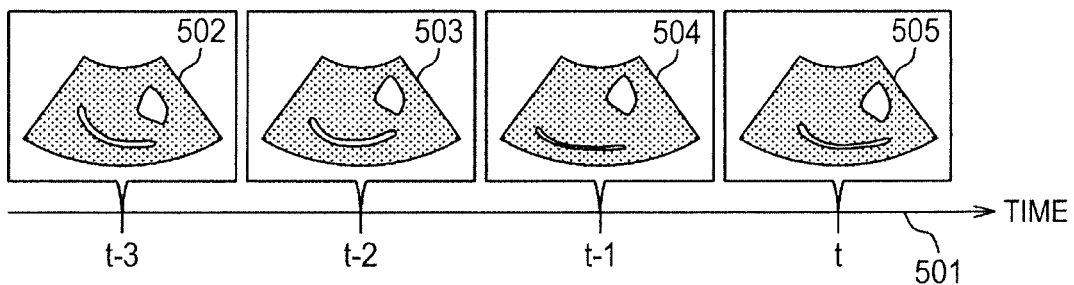
FIG. 5A is a front view of ultrasound images that are obtained by converting ultrasound images acquired at times t−3, t−2, t−1 and t into fan-shaped images with a scan converter by employing the configuration shown in FIG. 2.
Figure 5B:
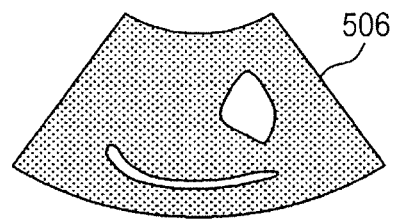
FIG. 5B is a front view of an ultrasound image showing an example of the result of the image reconstruction process executed to the ultrasound image 502-505 shown in FIG. 5A.

An examples of the resolution enhancement of an ultrasound images according to the process flow of FIG. 4 is shown in FIGS. 5A-5D. In FIG. 5A, the images 502-505 are the ultrasound images acquired at times t−3, t−2, t−1 and t along the temporal axis 501, respectively. The reference character 506 in FIG. 5B represents the image obtained by performing the resolution enhancement on the ultrasound image 505 (acquired at the time t) by the image reconstruction process by using the images 502-505 shown in FIG. 5A. In this example, the image data acquired from the ultrasound probe 103 are converted by the scan converter 112 into fan-shaped images and the process is executed by using the fan-shaped images (obtained by the conversion) as the ultrasound images (an example of the process in the device configuration shown in FIG. 2).

Figure 5C:
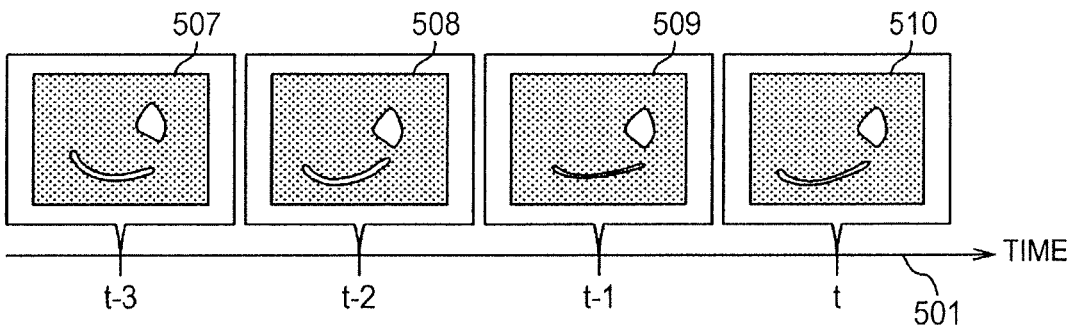
FIG. 5C is a schematic diagram showing an example of the result of the image reconstruction process (before the scan converter) executed to ultrasound images acquired at times t−3, t−2, t−1 and t by employing the configuration shown in FIG. 1.
Figure 5D:
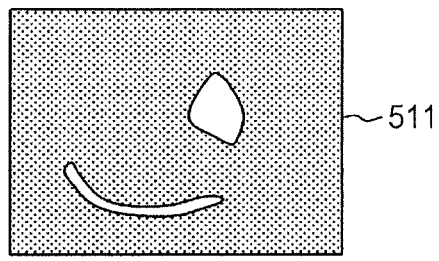
FIG. 5D is a front view of an ultrasound image showing an example of the result of the image reconstruction process executed to the ultrasound image 507-510 shown in FIG. 5C.

This example is also applicable to the device configuration shown in FIG. 1. In this case, a high-resolution ultrasound image 511 (before the scan converter) shown in FIG. 5D is generated from ultrasound images 507-510 (before the scan converter) shown in FIG. 5C. Similarly to the above explanation referring to FIGS. 5A and 5B, the images 507-510 in FIG. 5C are ultrasound images acquired at times t−3, t−2, t−1 and t along the temporal axis 501, respectively, and the reference character 511 in FIG. 5D represents the image obtained by performing the resolution enhancement on the ultrasound image 510 (acquired at the time t) by the image reconstruction process by using the images 507-510 shown in FIG. 5C. By performing the coordinate transformation process and the interpolation process with the scan converter 112, the high-resolution ultrasound image 511 obtained by the resolution enhancement can be converted into the fan-shaped image shown in FIG. 5B and displayed on the screen of the display unit 113.

An example of conducting region splitting to the ultrasound images based on the magnitudes of positional shifts between images and setting a weighting parameter of the image reconstruction process for each of the split regions is shown in FIGS. 6A-6E. This example is characterized in that an image in a region (regional image) having a larger weighting parameter is reflected more into the result of the image reconstruction process. For example, a point where the magnitude of positional shift is large has a high probability that parts around the point have deformed significantly, and thus there are cases where executing the image reconstruction process by compensating for the deformation is difficult. In such cases, regions in which the positional shift compensation is difficult are assigned small weighting parameters according to the present embodiment. In such regions, the image data of the processing object image becomes dominant. Thus, according to the present embodiment, regions in which the image reconstruction process is highly effective can be extracted automatically and the resolution enhancement can be performed on such regions even in the observation of a part moving fast (e.g., heart).

Figure 6A:
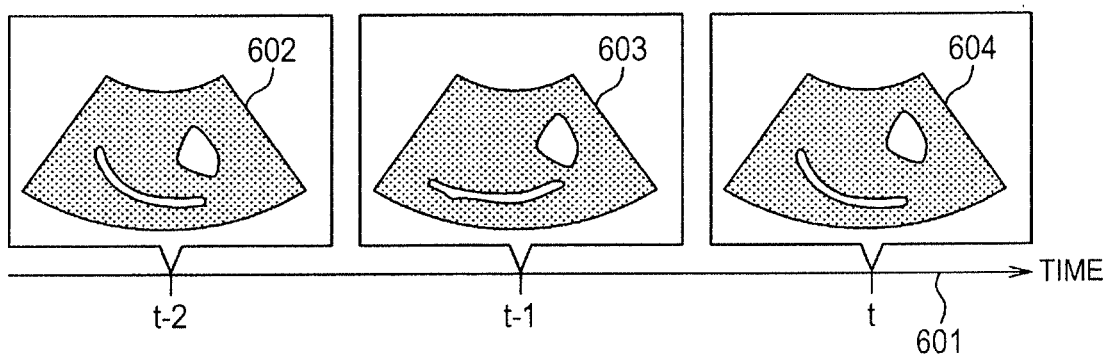
FIG. 6A is a front view of ultrasound images that are obtained by converting ultrasound images acquired at times t−2, t−1 and t into fan-shaped images with the scan converter by employing the configuration shown in FIG. 2.

The reference characters 602-604 in FIG. 6A represent ultrasound images captured along the temporal axis 601. In this case, the ultrasound image 604 is assumed to be the processing object image. The reference character 605 in FIG. 6E represents the result of the calculation of the magnitudes of positional shifts between the ultrasound images 604 and 603. Each arrow 615 indicates the direction and the magnitude of the positional shift. The reference characters 606-608 in FIG. 6E represent the result of the splitting into three regions based on the magnitudes of positional shifts. The region 607 is the region in which the positional shift is the largest, while the region 606 is the region in which the positional shift is the smallest. The reference characters 609 in FIG. 6B, 610 in FIG. 6C and 611 in FIG. 6D represent the result of setting the weighting parameters of the image reconstruction process based on the region splitting results 606-608 shown in FIG. 6E.

Figure 6B:
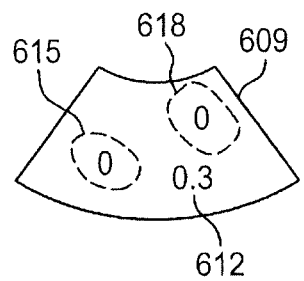
FIG. 6B is a schematic diagram showing a state in which region splitting has been performed based on the magnitudes of positional shifts and weighting parameters of the image reconstruction process have been set in an ultrasound image 602 acquired at time t−2.
Figure 6C:
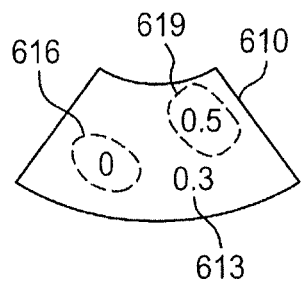
FIG. 6C is a schematic diagram showing a state in which the region splitting has been performed based on the magnitudes of positional shifts and the weighting parameters of the image reconstruction process have been set in an ultrasound image 603 acquired at time t−1.
Figure 6D:
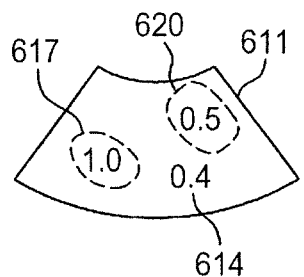
FIG. 6D is a schematic diagram showing a state in which the region splitting has been performed based on the magnitudes of positional shifts and the weighting parameters of the image reconstruction process have been set in an ultrasound image 604 acquired at time t.
Figure 6E:
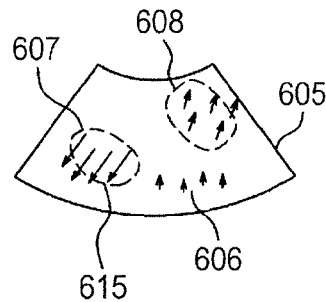
FIG. 6E is a schematic diagram showing the result of the calculation of the magnitudes of positional shifts between the ultrasound image 604 and 603.

In FIGS. 6B-6D, regions 612-614 in which the positional shift is small have been assigned weighting parameters 0.3, 0.3 and 0.4, respectively. This means that the images of the regions 612-614 shown in FIGS. 6B-6D are almost equally incorporated into the image reconstruction result in the image reconstruction process. For regions 615-617 in FIGS. 6B-6D in which the positional shift is large, the weighting parameter has been set at 0 except for the region 617 in FIG. 6D. This means that only the image of the region 617 in FIG. 6D is reflected into the image reconstruction result in the image reconstruction process in regard to the region 607 in FIG. 6E. Regions 618-620 in FIGS. 6B-6D have also been assigned the weighting parameters in a similar manner.

Here, the image reconstruction process taking the weighting parameters in consideration can be executed by minimizing the value of the following expression (2):

$$L(Y)=\Sigma_{i=1}^{N}|W_i(DF_PS_iY-X_i|+\gamma(|Y-T_xY|+|Y-T_yY|)) \quad (2)$$

"Wi" in the above expression represents an operation (effect) of multiplying by the weighting parameter of the i-th image. Incidentally, the region splitting may either be performed automatically based on the magnitudes of positional shifts as explained above or performed by use of regions specified by the user on a GUI.

Figure 17:
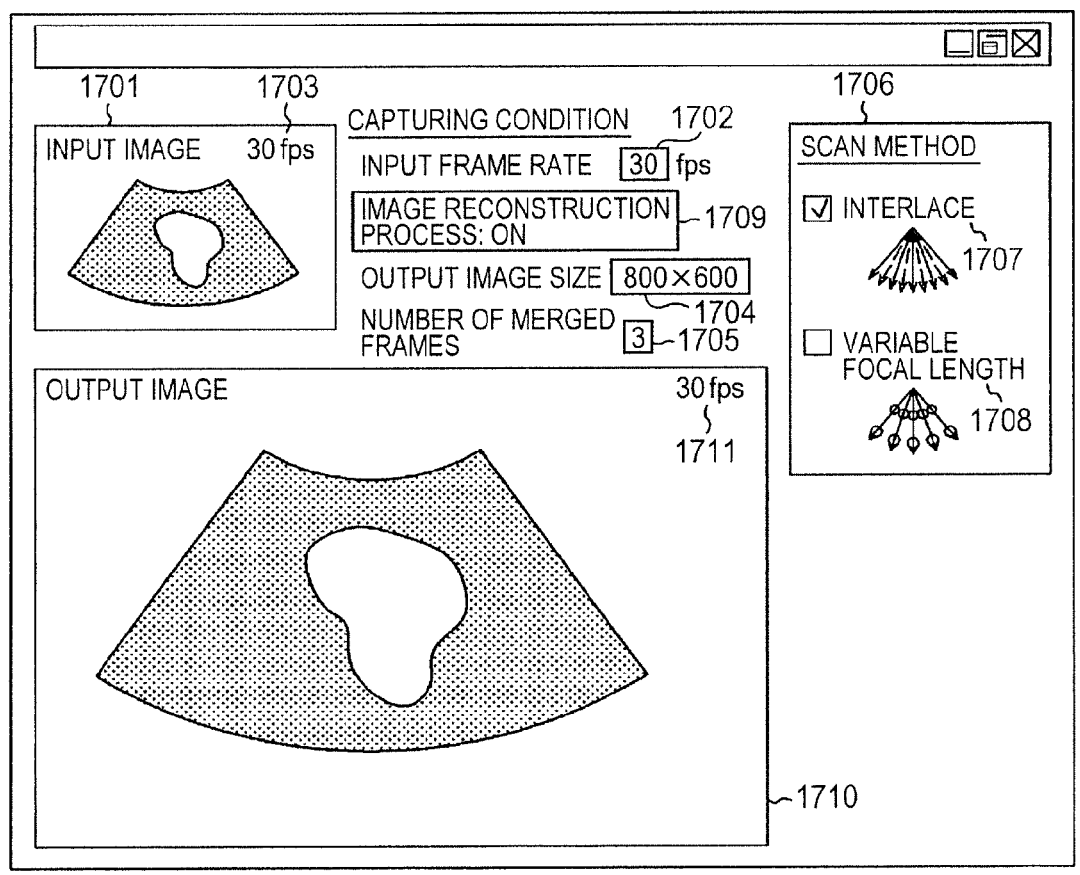
FIG. 17 is a schematic diagram showing a GUI used for executing the image reconstruction process to the ultrasound images (acquired by changing the scan condition from frame by frame) and for setting parameters of the image reconstruction process.

FIG. 17 shows an example of a GUI used in this example for generating the high-resolution ultrasound image from the ultrasound image group (acquired by changing the scan condition frame by frame) by the image reconstruction process, displaying the generated high-resolution ultrasound image in real time, and setting the scan condition and the image reconstruction process parameters. The window 1701 is displaying the ultrasound images captured by the ultrasound probe in real time. The image capturing frame rate is set by using the box 1702. The actual image capturing frame rate is displayed in the window 1701 as indicated by the reference character 1703. The parameters of the image reconstruction process are set by using the boxes 1704-1706.

The size of the output image after the image reconstruction process is set by using the box 1704. The number of frame images to be used for the image reconstruction process is specified by using the box 1705. The scan method is selected by using the box 1706. When the check box 1707 is selected, the image capturing is carried out by switching the scan orientation frame by frame by the interlace method. When the check box 1708 is selected, the image capturing is carried out while changing the focal length of the ultrasound beam frame by frame.

When the button 1709 is pressed by the user after setting the parameters of the image reconstruction process, the image reconstruction process is carried out. The high-resolution image obtained by the resolution enhancement by the image reconstruction process is displayed in real time in the window 1710. The display frame rate is displayed in real time as indicated by the reference character 1711.

Example 2

Figure 7:
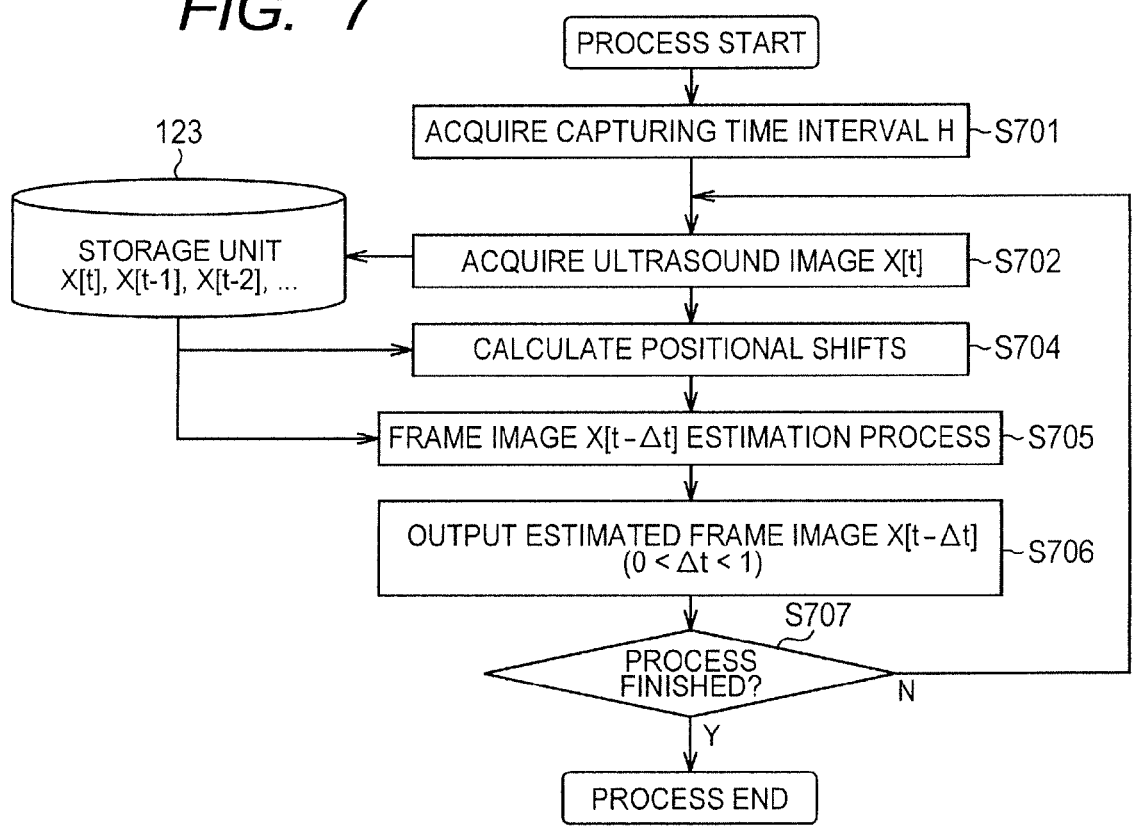
FIG. 7 is a flow chart for estimating an image of an intermediate frame on the temporal axis from captured images.

A second example of the image reconstruction process in the present invention will be described below referring to a flow chart of FIG. 7. In this example, the frame rate is increased by estimating and displaying intermediate frame images between the acquired ultrasound images on the temporal axis. In other words, while the example 1 was a process for increasing the spatial resolution, this example 2 increases the resolution in the temporal direction by estimating frame images between the acquired frame images. By this example, the frame rate can be increased without decreasing the number of scans per frame (i.e., without deteriorating the spatial resolution of images).

At the start of this process flow, the capturing time interval H of the ultrasound images (image acquisition interval) is acquired (S701). The image acquisition interval H may either be given manually or figured out from the value of the requested frame rate. Subsequently, ultrasound images X[t], X[t−1], X[t−2], . . . are acquired by imaging the test object 100 with the ultrasound probe 103 along a time series at the image acquisition intervals (S702). The acquired frame images are stored in the storage unit 123. Subsequently, the magnitudes of positional shifts between images are calculated similarly to the example 1 (S704). Subsequently, based on the ultrasound images and the magnitudes of positional shifts, an ultrasound image that is supposed to be acquired by imaging the test object 100 with timing shifted from the capturing timing of the processing object image by a time shorter than the image acquisition interval (intermediate frame image) is estimated (S705) and outputted to the screen (S706). The sequence of steps S702-S706 is repeated depending on the result of a termination judgment (S707).

Figure 24:
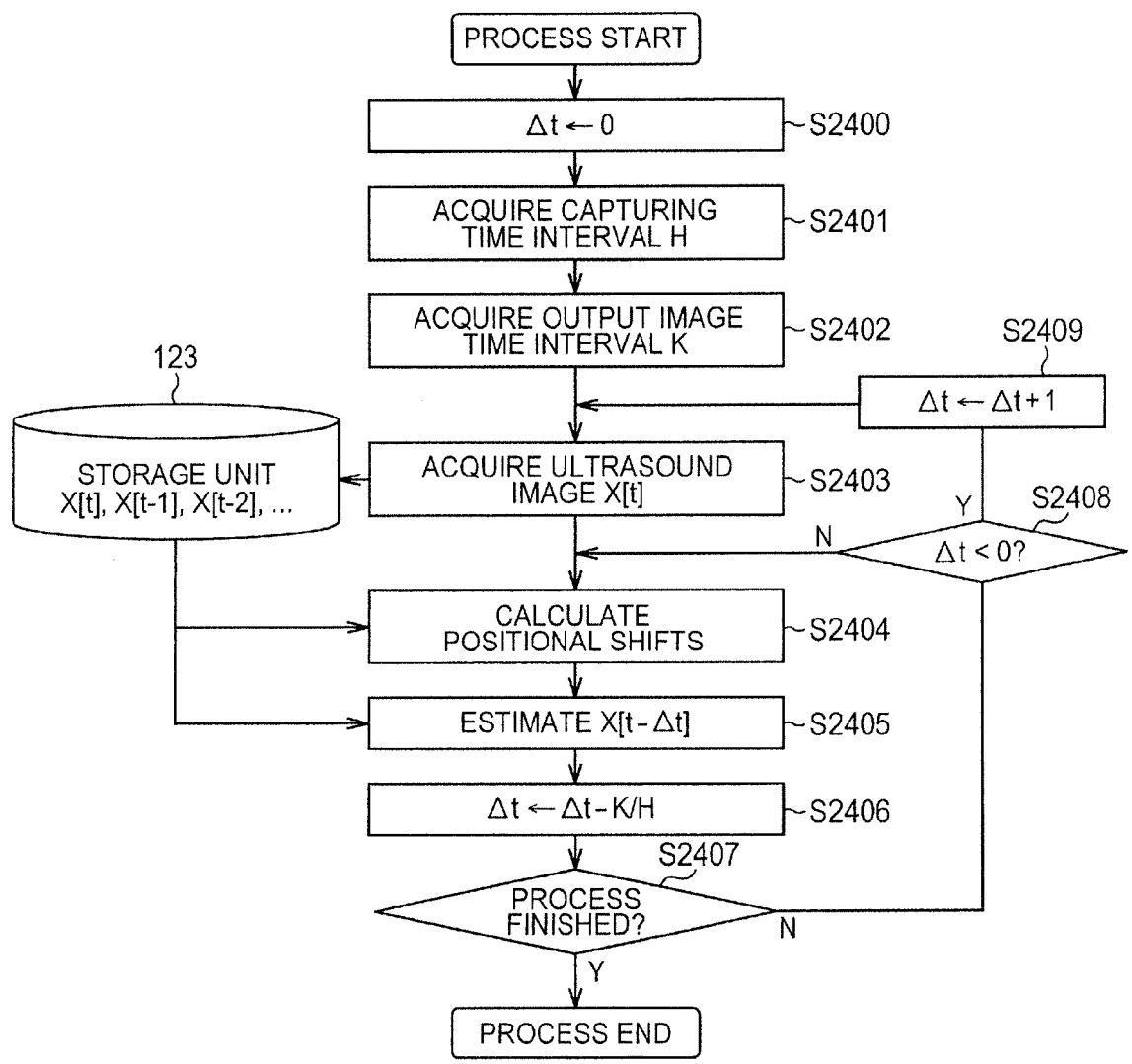
FIG. 24 is a flow chart for generating the intermediate frame image on the temporal axis from acquired ultrasound images.

FIG. 24 shows a flow in a case where the output frame rate is specified in this process. First, the shift width Δt of the intermediate frame image (the image to be estimated) on the temporal axis is initialized to 0 (S2400). Subsequently, the capturing time interval H of the ultrasound images is acquired (S2401). The capturing time interval H may either be set by use of a manually inputted value or figured out from an inputted frame rate. Subsequently, a time interval K of output images is acquired (S2402). Similarly to the capturing time interval H, the output image time interval K may either be set by use of a manually inputted value or figured out from the requested frame rate. Subsequently, an ultrasound image X[t] is acquired at the capturing time interval H and the time t is updated as t=t+1 (S2403). The acquired image is stored in the storage unit 123.

Subsequently, the magnitudes of positional shifts between images are calculated similarly to the flow of FIG. 7 (S2404), and the intermediate frame image X[t−Δt] is estimated based on the magnitudes of positional shifts and the ultrasound images stored in the storage unit 123 (S2405). In this step, the acquired ultrasound image can be outputted directly without estimating the intermediate frame image in cases where Δt=0 or Δt=1. Subsequently, the shift width Δt on the temporal axis is updated as Δt←Δt−K/H (S2406).

When the process is continued as a result of a process termination judgment (S2407: N), the sign of the shift width Δt on the temporal axis is judged (S2408). If the shift width Δt is a negative value, the shift width Δt is updated as Δt←Δt+1 (S2409) and the process advances to the ultrasound image X[t] acquisition step (S2403), otherwise the process advances to the positional shift calculation step (S2404).

Figure 8A:
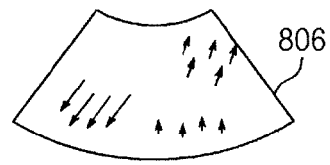
FIG. 8A is a schematic diagram showing the result of the calculation of the magnitudes of positional shifts between an ultrasound image 802 at time t−1 and an ultrasound image 803 at time t.
Figure 8B:
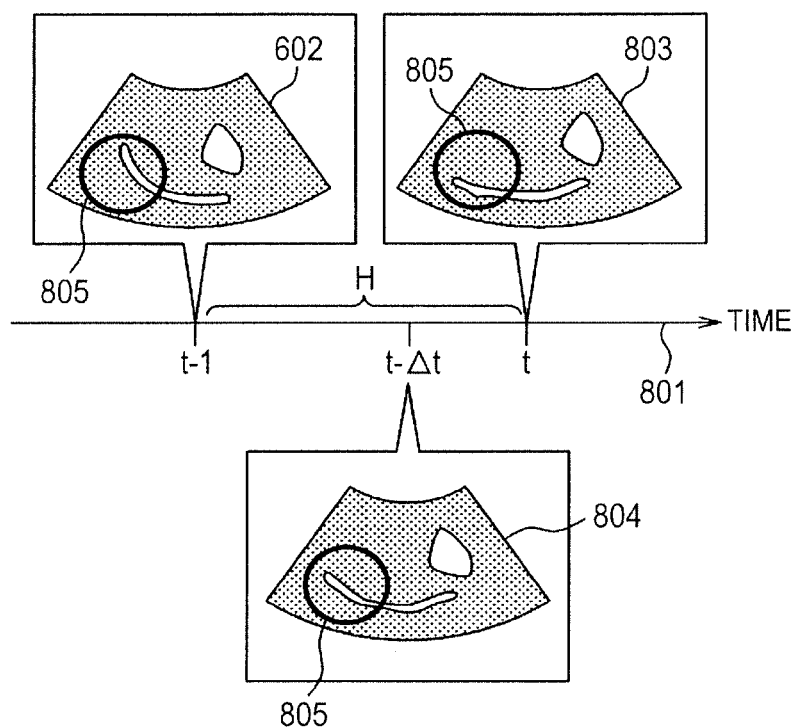
FIG. 8B shows front views of ultrasound images 802 and 803 obtained by converting ultrasound images acquired at times t−1 and t into fan-shaped images with the scan converter and an ultrasound image 804 of the intermediate frame estimated by the flow of FIG. 7.
Figure 8C:
FIG. 8C is a schematic diagram showing the magnitudes of positional shifts at time t−Δt estimated from the ultrasound images acquired at times t−1 and t.

An example of the result of the processing according to this flow is shown in FIGS. 8A-8C. The ultrasound images 802 and 803 in FIG. 8B are those captured at the image acquisition interval H along the temporal axis 801. The ultrasound image 804 is an image as the result of the estimation of the ultrasound image captured at time t−Δt (Δt≤1) from the ultrasound images 802 and 803. The linear-shaped part that can be seen in the region 805 in the ultrasound image 804 has moved from the upper left toward the lower right between the ultrasound images 802 and 803. The ultrasound image 804 has been estimated so that the linear-shaped part is situated at an intermediate position between the two positions in the ultrasound images 802 and 803.

As a method for estimating the intermediate frame image, the magnitudes of positional shifts between the time t and the time t−1 are calculated first as shown in FIG. 8A (806). Subsequently, the magnitudes of positional shifts at the time of the intermediate frame image (like the magnitudes of positional shifts shown in FIG. 8C) are estimated from the magnitudes 806 of positional shifts (807). This estimation can be performed simply by executing linear interpolation to the calculated magnitudes 806 of positional shifts. Finally, the intermediate frame image 804 can be generated by conducting the merging or weighted addition to the pixels of the acquired ultrasound images 802 and 803 shown in FIG. 8B based on the estimated magnitudes of positional shifts.

Figure 19:
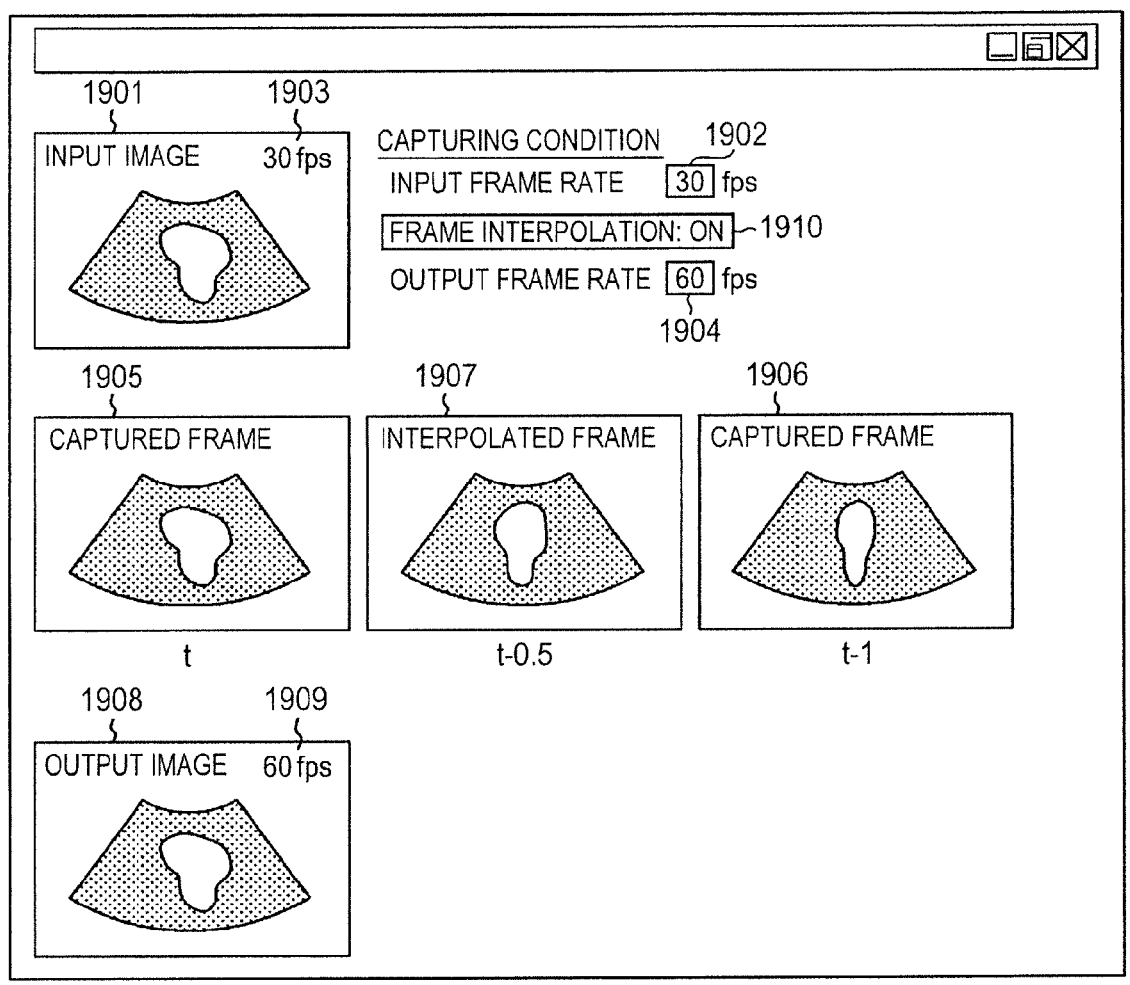
FIG. 19 is a schematic diagram showing a GUI used for a process for estimating an intermediate frame image on the temporal axis from captured images and for setting parameters.

FIG. 19 shows an example of a GUI used in this example for estimating the intermediate frame image on the temporal axis from the captured ultrasound images and thereby displaying ultrasound images at an increased frame rate. The window 1901 is displaying the ultrasound images captured by the ultrasound probe in real time. The image capturing frame rate is set by using the box 1902. The actual image capturing frame rate is displayed in the window 1901 as indicated by the reference character 1903. The frame rate of the output images is set by using the box 1904. This process is started when the button 1910 is pressed. The reference character 1905 represents a frame image acquired last (frame t). The reference character 1906 represents a frame image (frame t−1) acquired just before the frame image 1905. The reference character 1907 represents the image of the exactly intermediate frame on the temporal axis (frame t−0.5) estimated from the frame images 1905 and 1906. The images obtained by increasing the frame rate by the above process are displayed in the window 1908 together with the frame rate 1909.

Example 3

Figure 9:
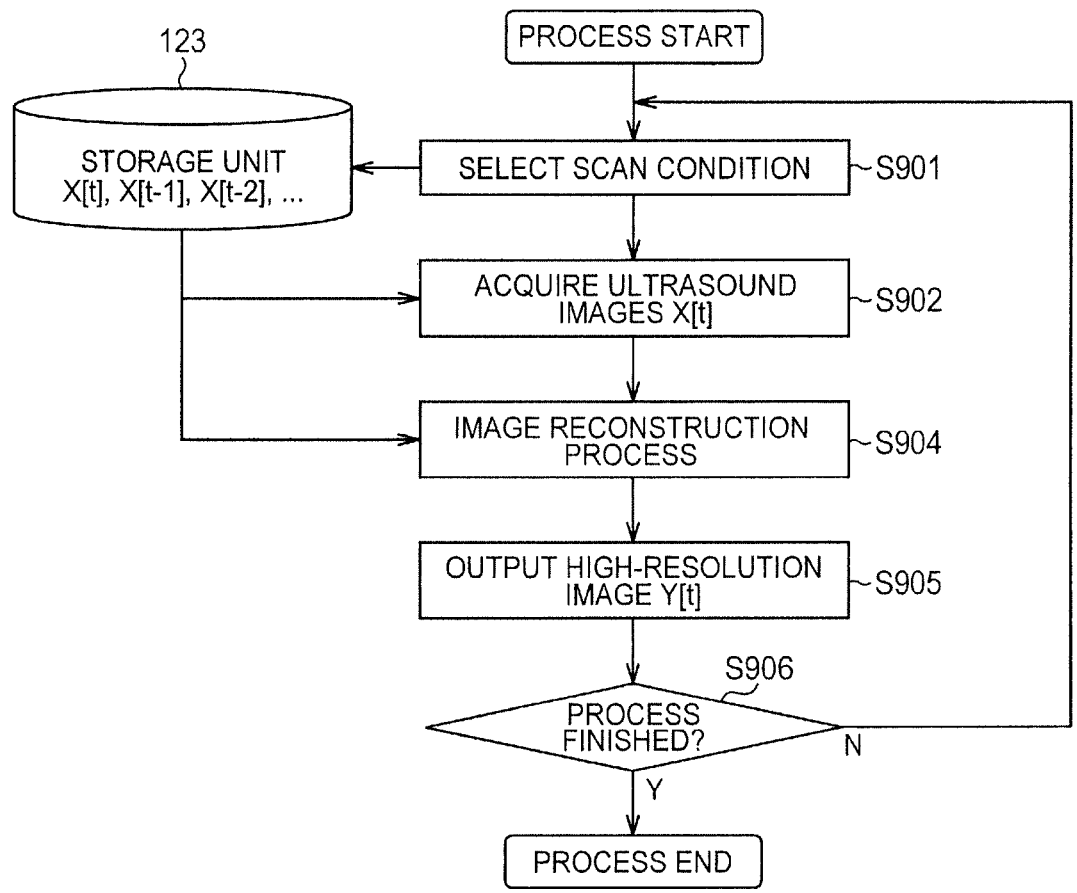
FIG. 9 is a flow chart for executing the image reconstruction process by using ultrasound images captured by changing the scan condition frame by frame.

A third example of the image reconstruction process in the present invention will be described below referring to a flow chart of FIG. 9. In this example, the image reconstruction process is executed more effectively by switching the scan condition of the ultrasound probe frame by frame. Since the image reconstruction process is a process of complementarily interpolating image information between frames, the resolution enhancement effect is weak if substantially identical images are inputted to the image reconstruction process.

In contrast, this example is characterized in that ultrasound images differing in the scan condition are acquired by controlling the ultrasound probe and the image reconstruction process is executed by using the ultrasound images acquired under different scan conditions. Specifically, changing the scan condition allows the ultrasound images to contain a substantial amount of complementary information, by which the resolution enhancement effect by the image reconstruction process can be increased.

At the start of this process flow, the scan condition of the ultrasound probe is set by selecting one from previously prepared scan conditions (S901). Selectable scan conditions may include the interlace method which alternately switches between image acquisition exclusively in even-numbered scan orientations and image acquisition exclusively in odd-numbered scan orientations frame by frame. In regions in which the movement is small, the resolution enhancement can be achieved just by simply overlaying two frame images acquired by the interlace method.

In contrast, when the movement is large, a positional shift called "jitter" can occur at the interfaces between frames. Also for such jitter, a compensation process can be conducted by using the magnitudes of positional shifts. In this method, the scan orientation switching and the image synthesis are possible also for three or more frames in a similar manner.

A method switching the scan focal length frame by frame can also be employed as another scan method. Specifically, if the focal point of the ultrasound beam during the scan is restricted to a particular position, the image of the other parts are blurred even though a sharp and clear image can be acquired for the particular position. Therefore, the tight-focused image area can be increased by merging (combining) multiple ultrasound images acquired by changing the scan focal length frame by frame.

Subsequently, an ultrasound image X[t] is acquired by imaging the test object 100 with the ultrasound probe 103 under the selected scan condition along a time series (S902). The acquired ultrasound images X[t], X[t−1], . . . are stored in the storage unit 123. Then, the high-resolution ultrasound image Y[t] of the ultrasound image X[t] is generated from the ultrasound images by the image reconstruction process (S904) and displayed (S905). Incidentally, this example is capable of increasing the spatial resolution of images without deteriorating the frame rate since the number of scans per frame is not increased in this example.

Figure 10A:
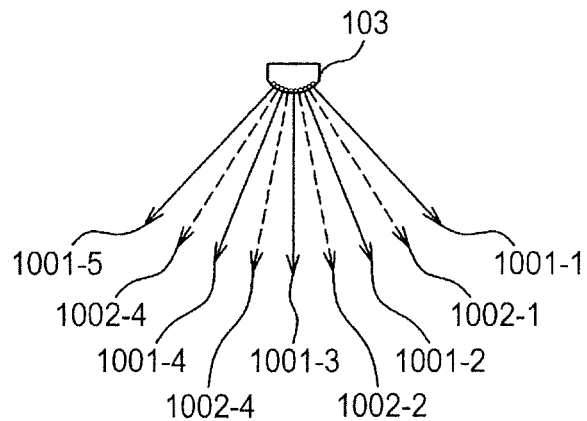
FIG. 10A is a cross-sectional view of the ultrasound probe showing the changing of the scan orientation frame by frame.
Figure 10B:
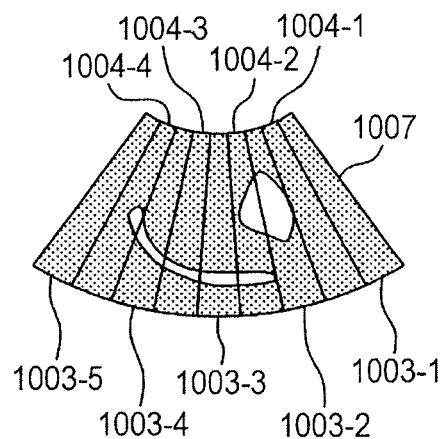
FIG. 10B is a front view of an ultrasound image after the scan converter, showing an example of merging images captured by changing the scan orientation frame by frame in the flow of FIG. 9.
Figure 10C:
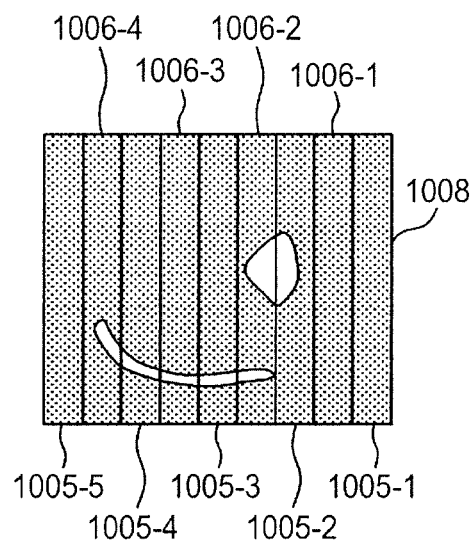
FIG. 10C is a front view of an ultrasound image before the scan converter, showing an example of merging images captured by changing the scan orientation frame by frame in the flow of FIG. 9.

An example of the scan orientation switching and the result of this process flow are shown in FIGS. 10A-10C. In this example, one frame image is generated from two frame images differing in the scan orientation. In FIG. 10A, the scan orientations 1001-1-1001-5 are those of ultrasound beams emitted from the ultrasound probe 103 for the first frame, while the scan orientations 1002-1-1002-4 are those of ultrasound beams emitted from the ultrasound probe 103 for the second frame. In FIG. 10B, the partial images 1003-1-1003-5 represent image data acquired by the scan for the first frame, while the partial images 1004-1-1004-4 represent image data acquired by the scan for the second frame. As illustrated in this example, an ultrasound image 1007 with an improved resolution with respect to the azimuth direction can be obtained by complementarily synthesizing image information on each frame by integrating the image data of two frames.

The ultrasound image 1007 can be generated either by use of the image reconstruction process by determining the magnitudes of positional shifts between images similarly to the example 1 or by simply conducting averaging (arithmetic mean). For the third frame, an ultrasound image with an enhanced resolution can be generated similarly to the case of the first frame, by emitting ultrasound beams in the scan orientations 1001-1-1001-5 shown in FIG. 10A and integrating image data acquired in the second frame and the third frame. Incidentally, while the ultrasound image 1007 shown in FIG. 10B is obtained by executing this process by use of ultrasound images after the scan converter in the system configuration shown in FIG. 2, this process may also be executed by use of ultrasound images before the scan converter by employing the system configuration shown in FIG. 1.

The reference character 1008 in FIG. 10C represents an example of applying this process to ultrasound images before the scan converter. In this example, the high-resolution ultrasound image 1008 is obtained by acquiring image data of the partial images 1005-1-1005-5 in the first frame, acquiring image data of the partial images 1006-1-1006-4 in the second frame, and merging the image data acquired in the first frame and the image data acquired in the second frame. While this explanation has been given for two frames, this process can also be executed for three or more frames in a similar manner.

Figure 11:
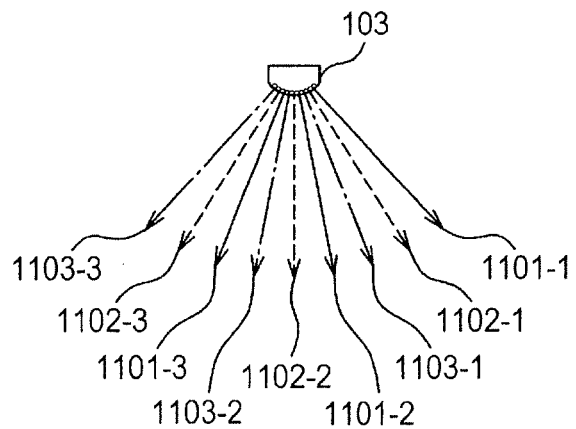
FIG. 11 is a cross-sectional view of the ultrasound probe showing an example of changing the scan orientation for three frames.

FIG. 11 shows an example of the process for three frames. In example, the scan orientations 1101-1-1101-3 are those for the first frame, the scan orientations 1102-1-1102-3 are those for the second frame, and the scan orientations 1103-1-1103-3 are those for the third frame.

Figure 13A:
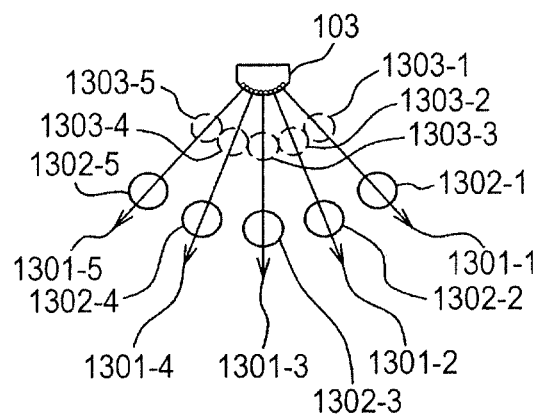
FIG. 13A is a cross-sectional view of the ultrasound probe showing a state in which the scan focal length is changed frame by frame.
Figure 13B:
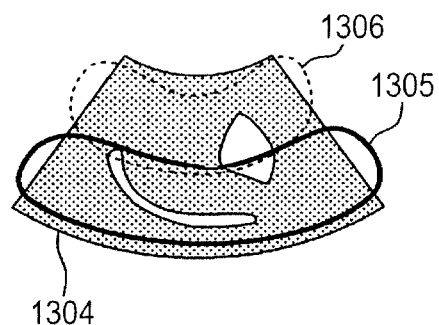
FIG. 13B is a front view of an ultrasound image showing an example of merging images captured by changing the scan focal length frame by frame.

While the scan orientation was changed frame by frame in the examples explained referring to FIGS. 10A-10C, an example of acquiring ultrasound images by changing the focal length of the ultrasound beam frame by frame in the scan is shown in FIGS. 13A and 13B. In this example, while the ultrasound beam is emitted in the scan orientations 1301-1-1301-5 shown in FIG. 13A, ultrasound images are acquired in the first frame by focusing the ultrasound beam on the positions of the circles 1302-1-1302-5, and in the second frame by focusing the ultrasound beam on the positions of the circles 1303-1-1303-5.

Specifically, in an ultrasound image like the one shown in FIG. 13B, the lower region 1305 becomes sharp and clear but the upper region 1306 becomes blurry in the first frame. Similarly, in the second frame, the lower region 1305 of the ultrasound image becomes blurry but the upper region 1306 becomes sharp and clear. As above, the ultrasound beam has a characteristic in that focusing the ultrasound beam on one point leads to the blurring of the other parts in the acquired image. Thus, the focal point of the ultrasound beam is generally set substantially at the center of the image so that the whole image becomes sharp and clear on the average. In contrast, in the present invention, ultrasound images are acquired by actively changing the focal position and the acquired ultrasound images are integrated together. This makes it possible to acquire a sharp and clear ultrasound image that is tight-focused throughout the whole image.

Figure 14A:
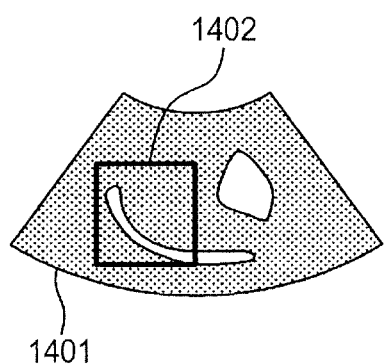
FIG. 14A is a front view of an ultrasound image showing an example of a region to be scanned densely specified by the user on the ultrasound image.
Figure 14B:
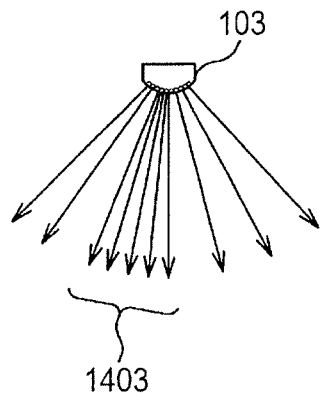
FIG. 14B is a cross-sectional view of the ultrasound probe showing an example of densely scanning the region specified by the user.

This process can also be applied exclusively to a region specified by the user as shown in FIGS. 14A and 14B. In the ultrasound image 1401 shown in FIG. 14A, the reference character 1402 represents the region (ROI) specified by the user. In this case, it is possible to capture ultrasound images by controlling the ultrasound probe 103 and concentrating the scan orientations in the ROI 1402 shown in FIG. 14A, like the scan orientations 1403 shown in FIG. 14B.

This process can also be employed together with the multi-beam method in which signals are received by simultaneously emitting ultrasound beams in two orientations or an ultrasound beam is emitted in another orientation before a signal is received by emitting an ultrasound beam in one orientation.

Figure 18:
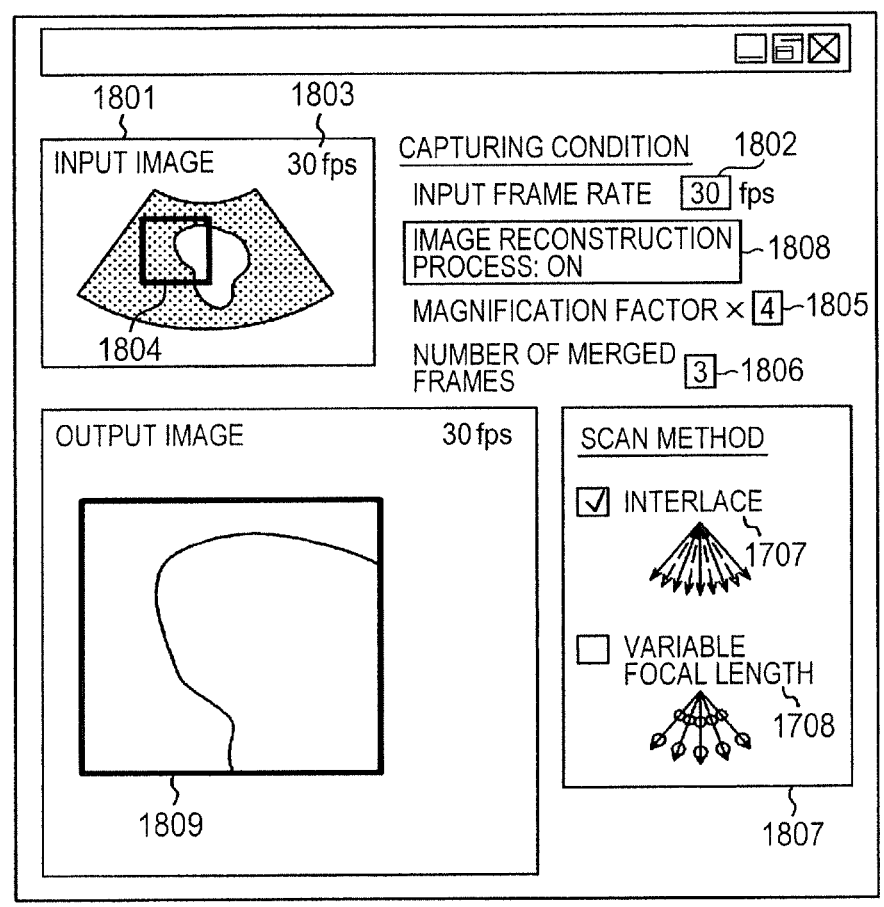
FIG. 18 is a schematic diagram showing a GUI used for a process for enhancing the resolution of a region specified by the user and for setting parameters.

FIG. 18 shows an example of a GUI used in this example for enhancing the resolution of a region specified by the user (ROI) and displaying the resolution-enhanced image. The window 1801 is displaying the ultrasound images captured by the ultrasound probe in real time. The image capturing frame rate is set by using the box 1802. The actual image capturing frame rate is displayed in the window 1801 as indicated by the reference character 1803. The reference character 1804 represents the region ROI specified by the user by the mouse clicking, etc. The parameters of the image reconstruction process are set by using the boxes 1805-1807. The image magnification factor by the image reconstruction process is set by using the box 1805. The number of frame images to be used for the image reconstruction process is specified by using the box 1806. The scan method is selected by using the box 1807. When the button 1808 is pressed, the image reconstruction process is executed exclusively to the inside of the ROI 1804 and an image with an enhanced resolution is displayed in the window 1809. Incidentally, it is also possible to concentrate the scan exclusively in the specified ROI and display only the image of the ROI with an enhanced resolution.

Example 4

A fourth example of the image reconstruction process in the present invention will be described below referring to a flow chart of FIG. 15. In this example, ultrasound images of a test object that moves periodically (e.g., heart) are acquired by controlling the ultrasound probe by using cycle information on the periodically moving test object. From the ultrasound images which have been captured for two cycles or longer, high-resolution ultrasound images for a shorter time range (e.g., one cycle) are generated by employing the image reconstruction process. Since a part like the heart repeats periodical movement, ultrasound images of such a part captured at times at the same temporal phase in the repeated cycles become substantially identical with each other. Thus, for the same reason as that described in the example 3, the resolution enhancement effect cannot be expected so much even if a lot of substantially identical images are inputted to the image reconstruction process.

In contrast, the image capturing of the aforementioned object image and that of the aforementioned past object image in the present example are carried out under different scan conditions by changing the scan condition, by which the ultrasound images are allowed to contain a substantial amount of complementary information and the resolution enhancement effect by the image reconstruction process can be increased.

At the start of this process flow, the cycle T of the movement of the test object 100 is acquired (S1501). The cycle T may either be given manually or calculated automatically from ultrasound images acquired by imaging the test object 100 for a certain time range. Subsequently, the scan condition of the ultrasound probe is set by selecting one from previously prepared scan conditions (S1502). The scan orientation, the scan range, the scan focal length, etc. can be changed as the selectable scan condition similarly to the example 3. Subsequently, ultrasound images of the test object 100 are acquired along a time series by using the ultrasound probe 103 for two cycles or longer by changing the scan condition frame by frame (S1503).

The scan orientation, the scan range, the scan focal length, etc. can be changed as the scan condition. The acquired images are stored in the storage unit 123. As for the timing for changing the scan condition, the scan condition may either be changed cycle by cycle or frame by frame as long as the scan condition differs between two ultrasound images that are one cycle apart from each other. When a termination judgment step (S1505) judges that the image capturing has not finished, the scan condition selecting step (S1502) and the ultrasound image acquiring step (S1503) are repeated as a loop. After finishing the image capturing, the ultrasound images are inputted to the image reconstruction process, by which high-resolution ultrasound images are generated (S1506) and displayed (S1507).

Figure 15:
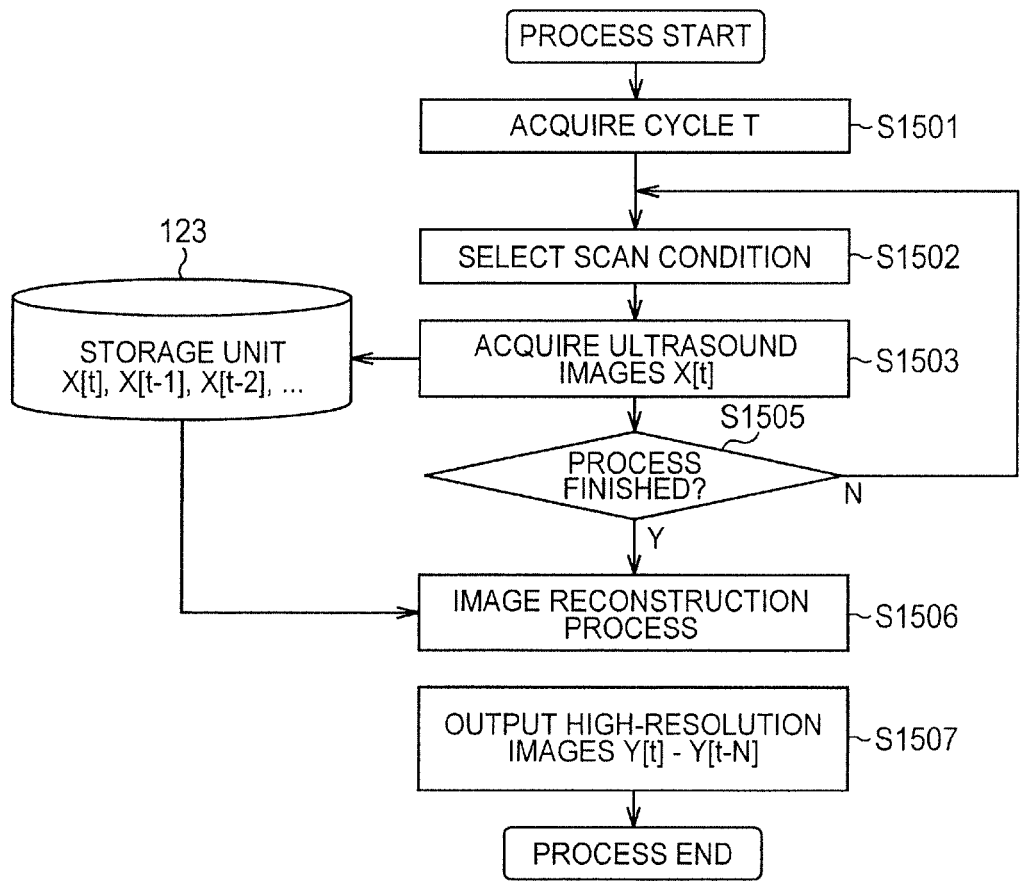
FIG. 15 is a flow chart for executing the image reconstruction process by using ultrasound images captured by changing the scan condition frame by frame by taking advantage of periodicity of the movement of the test object.
Figure 16:
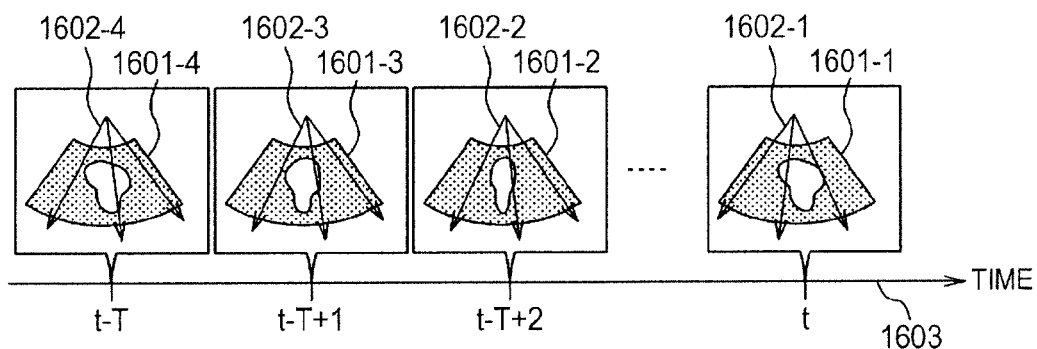
FIG. 16 is a front view of ultrasound images showing an example of capturing iso-phase frame images (frame images having the same temporal phase in cycles) under different scan conditions.

FIG. 16 shows an example of periodically changing the scan orientation for a periodically moving test object according to the flow of FIG. 15. The ultrasound image 1601-1 is a frame image acquired at time t. The ultrasound image 1601-4 is a frame image acquired one cycle T before the ultrasound image 1601-1. The ultrasound image 1601-3 is a frame image acquired at time t−T+1. The ultrasound image 1601-2 is a frame image acquired at time t−T+2. The reference characters 1602-1-1602-4 represent the scan orientations at the times of acquisition of the ultrasound images 1601-1-1601-4, respectively.

Figure 12A:
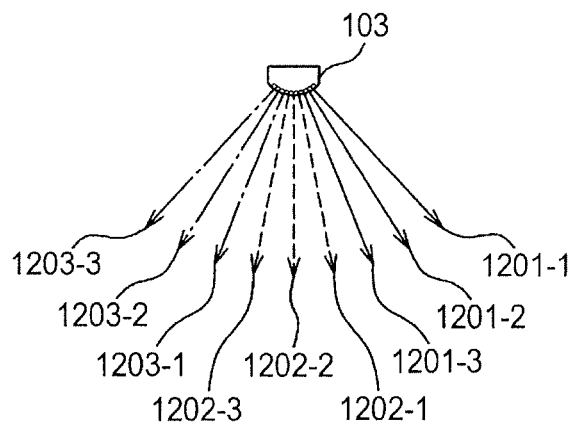
FIG. 12A is a cross-sectional view of the ultrasound probe showing a state in which the scan range is changed frame by frame.

FIG. 12A shows an example of acquiring and synthesizing images of a periodically moving test object by changing the scan range cycle by cycle according to the flow of FIG. 15. The scan orientations 1201-1-1201-3 are those at time t. The scan orientations 1202-1-1202-3 are those one cycle before the scan orientations 1201-1-1201-3. The scan orientations 1203-1-1203-3 are those two cycles before the scan orientations 1201-1-1201-3.

Figure 12B:
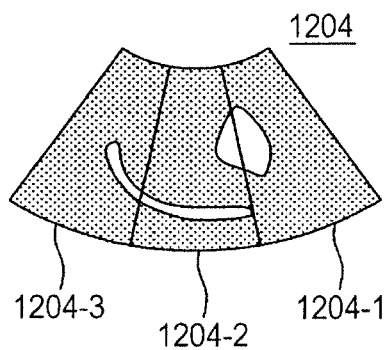
FIG. 12B is a front view of an ultrasound image showing an example of merging images captured by changing the scan range frame by frame.

In FIG. 12B, the partial image 1204-1 is an ultrasound image acquired with the scan orientations 1201-1-1201-3, the partial image 1204-2 is an ultrasound image acquired with the scan orientations 1202-1-1202-3, and the partial image 1204-3 is an ultrasound image acquired with the scan orientations 1203-1-1203-3.

One high-resolution ultrasound image 1204 can be generated by coupling the partial images 1204-1-1204-3 together. In this image coupling, it is possible to calculate the average (arithmetic mean) for parts where images overlap with each other or to execute a correction process to the interfacial parts (where images are coupled together) with a diffusing filter (blurring filter) or the like so that the images are connected seamlessly at the interface.

Figure 20:
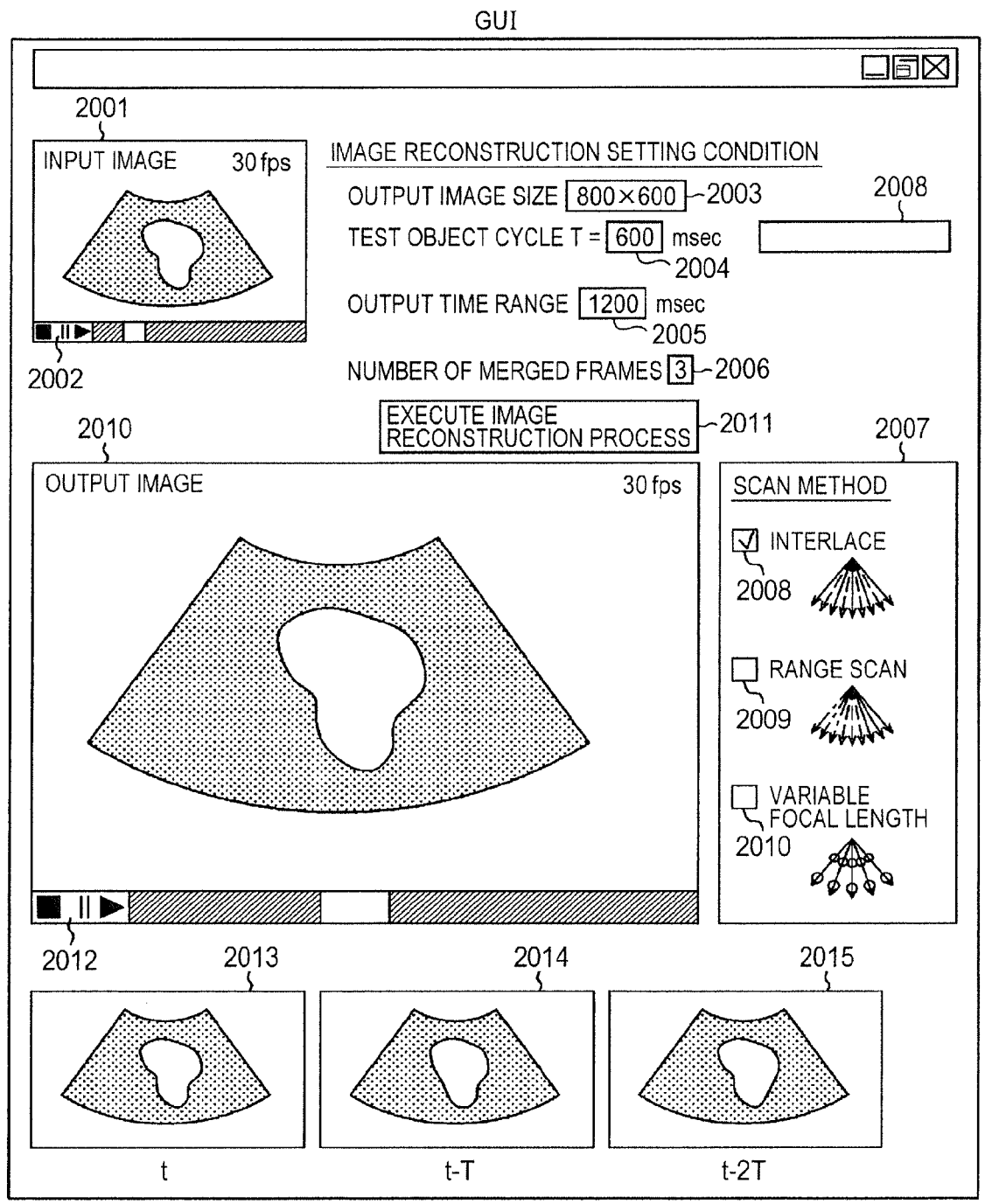
FIG. 20 is a schematic diagram showing a GUI used for executing the image reconstruction process to ultrasound images captured by changing the scan condition by taking advantage of the cycle of the movement of the test object and for setting parameters.

FIG. 20 shows an example of a GUI used in this example for executing the image reconstruction process by using ultrasound images captured by changing the scan condition by taking advantage of the cycle of the movement of the test object. The process in this example is not a real-time process like those explained in the examples 1-3 but a process of generating a high-resolution ultrasound video offline from ultrasound images (input ultrasound video) acquired by imaging the test object for a certain time range.

The reference character 2001 represents the ultrasound video as the object of the processing. The user can preview the ultrasound video 2001 by using the tool bar 2002 for starting/stopping the playback, changing the playback position, etc. The reference characters 2003-2007 represent parameter setting items of the image reconstruction process.

The size of the output image (video) is set by using the box 2003. The cycle of the movement of the test object is set by using the box 2004. The cycle may either be given manually or calculated automatically from the input ultrasound video in response to the pressing of the button 2008 by the user. The time range of the output video of the image reconstruction process is set by using the box 2005. The number of frame images to be used for the image reconstruction process is set by using the box 2006.

The scan method is selected by using the box 2007. When the check box 2008 is selected, the image capturing is carried out by switching the scan orientation frame by frame by the interlace method. When the check box 2009 is selected, the image capturing is carried out while changing the scan range frame by frame. When the check box 2010 is selected, the image capturing is carried out while changing the focal length of the ultrasound beam frame by frame. When the button 2011 is pressed by the user after setting the parameters of the image reconstruction process, the image reconstruction process is carried out.

The reference character 2010 represents the high-resolution ultrasound video outputted by the image reconstruction process. The user can preview the video by using the tool bar 2012 for starting/stopping the playback, changing the playback position, etc. The images 2013-2015 are input ultrasound images that are inputted to the image reconstruction process in regard to the currently displayed output image (video) 2010. The image 2014 is a frame image one cycle before the currently displayed output image 2010. The image 2015 is a frame image two cycles before the currently displayed output image 2010.

Incidentally, while some examples in accordance with the present invention have been described above, the present invention is not to be restricted to the above particular illustrative examples but can be implemented in a variety of modified forms.

APPENDIX 1

As described above, the present invention provides an ultrasound image reconstruction method for reconstructing an ultrasound image of a sample by processing ultrasound images acquired from a signal generated by scanning the sample with an ultrasound signal by use of an ultrasound probe and receiving a reflected wave from the sample, comprising the steps of: extracting an ultrasound frame image at a certain time point and an ultrasound frame image at a time point before the certain time point from a series of ultrasound frame images constituting the ultrasound images acquired by the imaging; calculating magnitudes of positional shifts between the extracted ultrasound frame image at the certain time point and the extracted ultrasound frame image at the time point before the certain time point; and reconstructing a composite ultrasound image for one frame by compensating for the positional shifts between the extracted ultrasound frame image at the certain time point and the extracted ultrasound frame image at the time point before the certain time point by use of information on the calculated magnitudes of positional shifts and merging the extracted ultrasound frame image at the certain time point and the extracted ultrasound frame image at the time point before the certain time point together.

APPENDIX 2

The present invention also provides the ultrasound image reconstruction method as written in the appendix 1, wherein the ultrasound frame image at the certain time point and the ultrasound frame image at the time point before the certain time point are ultrasound images acquired in states differing in the scan condition for the scanning of the sample with the ultrasound signal by use of the ultrasound probe.

APPENDIX 3

The present invention also provides the ultrasound image reconstruction method as written in the appendix 1, wherein the ultrasound frame image at the certain time point and the ultrasound frame image at the time point before the certain time point are ultrasound images acquired by performing the scan in states differing in at least one of the scan orientation and the scan focal length for the scanning of the sample with the ultrasound signal by use of the ultrasound probe.

APPENDIX 4

The present invention also provides the ultrasound image reconstruction method as written in the appendix 1, wherein the merging of the ultrasound frame image at the certain time point and the ultrasound frame image at the time point before the certain time point after undergoing the positional shift compensation is executed by splitting each of the ultrasound frame image at the certain time point and the ultrasound frame image at the time point before the certain time point into local regions, setting a weighting parameter varying from region to region for each of the locally split regions, and incorporating each region into the image reconstruction process so that a region having a greater weight is incorporated more into the result of the image reconstruction process.

APPENDIX 5

The present invention also provides the ultrasound image reconstruction method as written in the appendix 1, wherein a composite ultrasound image for one frame at a time point between the certain time point and the time point before the certain time point is estimated and generated by merging the extracted ultrasound frame image at the certain time point and the extracted ultrasound frame image at the time point before the certain time point after undergoing the positional shift compensation together.

APPENDIX 6

The present invention also provides the ultrasound image reconstruction method as written in the appendix 1, wherein: the sample is one that moves periodically, and the images acquired by the imaging are ultrasound images acquired by scanning the sample for a time longer than or equal to twice the cycle of the periodical movement of the sample under scan conditions varying cycle by cycle, and the extraction of the ultrasound frame image at the certain time point and the ultrasound frame image at the time point before the certain time point is extraction of the ultrasound frame image at the certain time point and an ultrasound frame image at a time point one cycle before the certain time point.

INDUSTRIAL APPLICABILITY

The present invention can be employed for ultrasound diagnostic devices which acquire images by transmitting and receiving an ultrasonic wave to/from a test object. In particular, the present invention can be employed for ultrasound diagnostic devices equipped with an ultrasound image reconstruction method for executing a process for enhancing the spatial resolution or the temporal resolution to acquired images by means of image processing.

DESCRIPTION OF REFERENCE CHARACTERS

100 test object
101 ultrasound diagnostic device
102 driving circuit unit
103 ultrasound probe
104 reception circuit unit
105 image generating unit
106 image processing unit
112 scan converter
113 display unit
120 control/storage/processing unit
121 input unit
122 control unit
123 storage unit
124 processing unit

What is claimed is:
1. An ultrasound diagnostic device comprising:
an image acquisition unit to acquire time-sequentially images in a predetermined interval from signals which receive a reflected wave from a sample scanned with an ultrasound signal by an ultrasound probe;
a displacement amount calculator to calculate a first displacement amount between neighboring time-sequentially images from a first image at a first time point and second image at a second time point which is before the first time point;
an intermediate image generator to generate an intermediate image at a certain time point between the second time point and the first time point, and the intermediate image is generated from the first image, the second image, and a second displacement amount at the certain time point calculated based on the first displacement; and
a display unit to subsequently display the second image, the intermediate image, and the first image, and
the first displacement amount and the second displacement amount are plural based on a difference of position, and are represented with a vector distribution.
2. The ultrasound diagnostic device according to claim 1, wherein a frame rate of images displayed at the display unit is higher than images acquired at the image acquisition unit.
3. The ultrasound diagnostic device according to claim 2, wherein the intermediate image is generated based of the first image entirely and the second image entirely,
and wherein the display unit subsequently displays the second image entirely, the intermediate image entirely, and the first image entirely.
4. The ultrasound diagnostic device according to claim 1, wherein the second displacement amount is calculated by linear interpolation.
5. The ultrasound diagnostic device according to claim 1, wherein the intermediate image generator generates the inter- mediate image by pasting pixels of the second image and the first image, or by subjecting the pixels to weighted summation.

6. The ultrasound diagnostic device according to claim 1, wherein the certain time point can be manually input.

7. The ultrasound diagnostic device according to claim 1, wherein the certain time point is calculated from a frame rate of images displayed at the display unit.

8. A method of generating an intermediate image of an ultrasound image comprising the steps of:
   first step of acquiring time-sequentially images in a predetermined interval from signals which receive a reflected wave from a sample scanned with an ultrasound signal by an ultrasound probe;
   second step of calculating a first displacement amount between neighboring time-sequentially images from a first image at a first time point and second image at a second time point which is before the first time point;
   third step of generating an intermediate image at a certain time point between the second time point and the first time point, and the intermediate image is generated from the first image, the second image, and a second displacement amount at the certain time point calculated based on the first displacement; and
   forth step of displaying the second image, the intermediate image, and the first image subsequently, and the first displacement amount and the second displacement amount are plural based on a difference of position, and are represented with a vector distribution.

9. The method of generating an intermediate image of an ultrasound image according to claim 8, wherein a frame rate of images displayed at a display unit is higher than images of the first step.

10. The method of generating an intermediate image of an ultrasound image according to claim 9, wherein the third step generates the intermediate image entirely by using a first image entirely and the second image entirely.

11. The method of generating an intermediate image of an ultrasound image according to claim 8, wherein the second displacement amount is calculated by linear interpolation.

12. The method of generating an intermediate image of an ultrasound image according to claim 8, wherein the third step pastes pixels of the second image and the first image, or subjects the pixels to weighted summation.

13. The method of generating an intermediate image of an ultrasound image according to claim 8, wherein the certain time point is manually inputted.

14. The method of generating an intermediate image of an ultrasound image according to claim 8, wherein the certain time point is calculated from a frame rate of images displayed at a display unit.

* * * * *